United States Patent
Barrett et al.

(10) Patent No.: US 10,705,081 B2
(45) Date of Patent: Jul. 7, 2020

(54) NANO-FIELD ELECTRICAL SENSOR

(71) Applicant: Sympano, Inc., Portland, OR (US)

(72) Inventors: Thomas W. Barrett, Portland, OR (US); Shalini Gautam, Hillsboro, OR (US); Rooplekha Mitra, Hillsboro, OR (US); James Thorne, Portland, OR (US)

(73) Assignee: SYMPANO, INC., Portland, OR (US)

( * ) Notice: Subject to any disclaimer, the term of this patent is extended or adjusted under 35 U.S.C. 154(b) by 275 days.

(21) Appl. No.: 15/694,784

(22) Filed: Sep. 2, 2017

(65) Prior Publication Data

US 2018/0067107 A1 Mar. 8, 2018

Related U.S. Application Data

(60) Provisional application No. 62/383,490, filed on Sep. 4, 2016.

(51) Int. Cl.
| | |
|---|---|
| *G01N 33/543* | (2006.01) |
| *C12Q 1/68* | (2018.01) |
| *G01N 27/07* | (2006.01) |
| *C12Q 1/6825* | (2018.01) |

(52) U.S. Cl.
CPC ....... *G01N 33/5438* (2013.01); *C12Q 1/6825* (2013.01); *G01N 27/07* (2013.01)

(58) Field of Classification Search
CPC ......... G01N 33/543; G01N 27/07; C12Q 1/68
USPC .............................. 422/82.01–82.03; 436/518
See application file for complete search history.

(56) References Cited

U.S. PATENT DOCUMENTS

| | | | | |
|---|---|---|---|---|
| 4,531,404 A | * | 7/1985 | Phelps | G01N 15/0806 277/614 |
| 4,963,245 A | * | 10/1990 | Weetall | G01N 27/3271 204/403.03 |
| 5,326,450 A | * | 7/1994 | Sugama | G01N 27/404 204/403.06 |
| 5,374,521 A | * | 12/1994 | Kipling | G01N 33/54373 310/312 |
| 5,384,028 A | * | 1/1995 | Ito | A61B 5/1486 204/403.11 |
| 5,755,953 A | * | 5/1998 | Henning | C12O 1/002 204/294 |
| 5,858,192 A | * | 1/1999 | Becker | B01J 19/0093 204/280 |
| 5,958,779 A | * | 9/1999 | Bonnick | G01N 27/423 204/409 |

(Continued)

OTHER PUBLICATIONS

Scampicchio, M. et al, Electroanalysis 2012, 24, 719-725.*

(Continued)

*Primary Examiner* — Arlen Soderquist
(74) *Attorney, Agent, or Firm* — McCoy Russell LLP

(57) ABSTRACT

Methods and compositions for the detection and quantitative measurement of biomarkers and other target analytes by determining impedance in bodily fluid samples and/or environmental samples using compositions comprising a base substrate with electrodes, a nanoporous membrane placed on top of the nanoporous membrane, O-rings placed on top of the nanoporous membrane and a manifold placed on top of the O-rings. Such a composition may be placed in a testing platform to ensure the application of constant, repeatable pressure to the composition.

8 Claims, 15 Drawing Sheets

(56) References Cited

U.S. PATENT DOCUMENTS

| | | | | |
|---|---|---|---|---|
| 5,961,799 | A * | 10/1999 | Matsumoto | G01N 27/3271 204/400 |
| 6,653,091 | B1 * | 11/2003 | Dunn | A61B 5/14532 204/400 |
| 6,670,115 | B1 * | 12/2003 | Zhang | G01N 33/5438 204/193 |
| 7,316,154 | B1 * | 1/2008 | Bennett | F16J 15/064 277/320 |
| 8,061,211 | B1 * | 11/2011 | Bennett | F16J 15/064 73/706 |
| 8,409,411 | B2 | 4/2013 | Prasad et al. | |
| 2004/0245101 | A1 * | 12/2004 | Willner | C12Q 1/004 204/403.01 |
| 2009/0050492 | A1 * | 2/2009 | Alocilja | C12Q 1/6825 205/782 |
| 2010/0051446 | A1 * | 3/2010 | Wang | B81C 1/0019 204/192.15 |
| 2011/0284374 | A1 * | 11/2011 | Krejci | B01L 3/5085 204/408 |
| 2012/0021934 | A1 * | 1/2012 | Morozov | G01N 33/54333 506/9 |
| 2013/0248378 | A1 * | 9/2013 | Kanemoto | G01N 27/30 205/641 |
| 2013/0327656 | A1 * | 12/2013 | Van Grinsven | C12Q 1/6825 205/780.5 |
| 2013/0334044 | A1 * | 12/2013 | Brown | G01N 27/414 204/433 |
| 2014/0015548 | A1 * | 1/2014 | Naughton | G01R 27/26 324/658 |
| 2015/0011421 | A1 * | 1/2015 | Li | G01N 27/27 506/11 |
| 2015/0114850 | A1 | 4/2015 | Prasad et al. | |
| 2015/0276637 | A1 | 10/2015 | Prasad et al. | |
| 2015/0355133 | A1 | 12/2015 | Prasad | |
| 2018/0252663 | A1 * | 9/2018 | Cabrera | G01N 27/3275 |

OTHER PUBLICATIONS

Barrett, T. et al., "Novel Nanomonitor ultra-sensitive detection of troponin T," Clinica Chimica Acta, vol. 442, Mar. 10, 2015, Published Online Jan. 23, 2015, 6 pages.

Selvam, A. et al., "Electrical nanowell diagnostics sensors for rapid and ultrasensitive detection of prostate-specific antigen," Nanomedicine (Lond.), vol. 10, No. 16, Aug. 21, 2015, 10 pages.

Shanmugam, N. et al., "Portable nanoporous electrical biosensor for ultrasensitive detection of Troponin-T," Future Science OA, vol. 1, No. 3, FSO24, Nov. 1, 2015, 10 pages.

* cited by examiner

NANO-FIELD ELECTRICAL SENSOR

CROSS REFERENCE TO RELATED APPLICATIONS

This application claims benefit of U.S. Provisional Patent Application No. 62/383,490 filed Sep. 4, 2016 entitled "Nano-Field Electrical Sensor", the entire contents of which are hereby incorporated by reference in its entirety for all purposes.

BACKGROUND

Biomarkers are a measurable indicator that may be used to precisely, reproducibly, and objectively reveal any molecular species found to provide correlation to a particular phenotype or perturbation of a biological system. For example, biomarkers may be used to distinguish a normal biological state from a pathological state. Biomarkers may also be used to detect a response to a specific therapeutic intervention (Biomarkers Definitions Working Group. Biomarkers and surrogate endpoints: preferred definitions and conceptual framework. Clin. Pharmacol. Ther. 69, 89-95 (2001)); to predict survival (prognostic biomarkers); to assess drug safety and evaluate target engagement and immediate consequence on biological processes (pharmacodynamics biomarkers); to identify patients who are more likely to benefit from a treatment (predictive or companion biomarkers when associated with a specific therapeutic agent); to predict outcome given the response to therapy (surrogate biomarkers); and to monitor disease progression or therapeutic efficacy (monitoring biomarkers) (Pragmatic issues in biomarker evaluation for targeted therapies in cancer. Armand de Gramont, Sarah Watson, Lee M. Ellis, Jordi Rodin, Josep Tabernero, Aimery de Gramont & Stanley R. Hamilton Nature Reviews Clinical Oncology 12, 197-212 (2015) doi: 1 0.1038/nrclinonc.2014.202). For example, biomarkers may be used to detect individuals who have a disease (e.g. cancer), infection (e.g. bacterial DNA, viral DNA, or antibody response), systemic breakdown (e.g. sepsis), environmental exposure (e.g. lead), are at risk for developing a disease (e.g. tuberculosis) or have experienced traumatic physiological event (e.g. heart attack).

Timely detection and quantification of disease biomarkers can be used to detect diseases at early stages of development, when they are frequently the most treatable or preventable. They are also increasingly necessary in personalized medicine, identifying the population of patients most likely to benefit from targeted therapies. Early identification of disease and target populations' most likely to benefit from treatment decreases mortality, cost, and in the case of infection, decreases the development of multi-drug resistant organisms. Point of care devices based on detection of biomarkers permit robust, low-cost and real-time rapid identification of a diseased state under a variety of conditions, allowing for enhanced monitoring and timely therapeutic changes.

In addition to biomarkers, there is a need for means for the rapid detection in small samples of other target analytes such as proteins, pathogens, heavy metal ions, small molecules, DNA, RNA, SNPs, microbes, agrochemicals, and hydrocarbons in environmental samples such as water, soil, food, beverages, building products, bulk chemicals or reagents. Current testing methods for biomarkers and analytes require large samples of the compound being tested. For example, standard samples for biomarker testing are at least 2 mL. Furthermore, current testing methods have limited sensitivity, requiring a relatively large amount of the biomarkers or analytes of interest to be present in order to be detected. There is therefore a need for compositions and methods for detecting small amounts of targets of interest in small samples.

BRIEF SUMMARY

Provided herein is a composition for detecting and/or quantifying a single or plurality of target analytes and biomarkers. The compositions described herein may be used with any useful device for measuring electrical impedance to detect and/or quantify the biomarkers and target analytes. As used herein, the terms analyte and biomarker may be used interchangeably to describe a target or targets to be detected and/or quantified. In some embodiments, the composition may be used with a testing platform. The testing platform may assist in performing repeatable, consistent identification and measurement of such target analytes in small quantities of bodily fluids or environmental samples.

The composition may comprise a nano-field electrical sensor comprising a biocompatible base substrate having a top surface onto which at least two electrodes in a capacitive relationship have been deposited. For example, in some embodiments, the electrodes may be a working electrode and a counter or auxiliary electrode. The composition may further comprise a nanoporous membrane (nanomembrane) placed on top of the electrodes and held in place by a manifold. In some embodiments, the composition may additionally comprise one or more O-rings placed between the nanoporous membrane and the manifold. In a further example at least one additional O-ring may be placed underneath the nano-field electrical sensor The nano-field electrical sensor (sensor) may include a biocompatible base substrate having a top surface on which one or more electrodes in a capacitive relationship have been deposited. The biocompatible base substrate may be any material generally used. In some embodiments, the biocompatible base substrate is a ceramic material with conductive properties such as alumina. The electrodes may be attached to the base substrate by any means generally used. For example, the electrodes may be placed on, etched on, sprayed on, or otherwise adhered to the base substrate. In some embodiments, the electrodes may be vapor deposited on the base substrate.

In one example, the biocompatible base substrate may have at least two electrodes plated on it. In some embodiments, the at least two electrodes are a working electrode and counter electrode. In additional embodiments, a reference electrode may additionally be placed on the base substrate in a capacitive relationship with the two other electrodes. The electrodes may be made of the same or different materials. For example, in some embodiments, the working electrode is gold. In further embodiments, the working electrode is silver. In additional embodiments, the counter electrode is silver. In yet another embodiment, the counter electrode is gold. In additional embodiments, a reference electrode may be used. In some embodiments, the reference electrode is gold. In other embodiments the reference electrode is silver. In further embodiments, the biocompatible base substrate may additionally comprise electrical connectors capable of connecting to exterior devices.

In some embodiments, a plain nanoporous membrane may be placed over the electrodes on the base substrate. In other embodiments, a functionalized nanoporous membrane may be placed over the electrodes on the base substrate. Both the plain and/or functionalized nanoporous membranes may have nanopores of a diameter between about 1 nm to about 2000 nm, about 2 nm to about 1000 nm, 2 nm to about 500 nm or any fraction thereof. In some examples the nanopores may average about 200 nm. The nanopores generally have variable sizes, though they may also be of the same size. In some embodiments, the nanopores may have a pattern of sizes. While the nanoporous membrane may be of any suitable conductive or non-conductive material such as nitrocellulose, nylon, silicon or paper, in some embodiments the nanoporous membrane is an electrospun polyamide nanofiber. In some embodiments the electrospun polyamide nanoporous membrane may be a nylon 6 electrospun fiber with a weight of 70 g/m$^2$, displaying high porosity and high specific surface area suitable for a range of applications including high efficiency filtration. Additionally, the electrospun nanoporous membrane may be non-conducting and display variable wettability, such that they may be used for a wide range of liquid analytes. Optionally, surface modifications (e.g. nanoparticle coating, treatment with heat, other chemicals) may further alter the surface characteristics and improve membrane performance, for example the nylon 6 electrospun fiber may be spun bonded with a PET (polyester) having a total thickness 0.34 mm. The composition and porosity of the electrospun polyamide fiber may be varied as required for the analyte being detected.

A manifold may be placed over the nanoporous membrane to hold the nanoporous membrane in place over the one or more (in some embodiments at least two) electrodes on the biocompatible base substrate. In some embodiments, the biocompatible manifold is a metal such as alumina. In other embodiments, the manifold may be ceramic with a metal such as alumina plated on it. In additional examples, the manifold may be any clear polymer such as, but not limited to, polydimethylsiloxane (PDMS) or acrylic. The biocompatible manifold may have one or more openings, generally at least two openings on its surface allowing fluid to be micropipetted in such a fashion as to reach the nanoporous membrane. Such openings may be of any size large enough to allow a sample and/or functionalization molecule to wick through to the nanoporous membrane. The openings in the manifold may have any cross-section desired. In some embodiments, the openings may be circular, triangular, rectangular and the like. The openings may have the same or different cross shapes.

In some embodiments, one or more O-rings may be placed between the nanoporous membrane and the manifold. Constant pressure is then used to hold the manifold in place on top of the nanoporous membrane and base substrate. While not wishing to be bound, it is currently theorized that the flexibility of the O-ring allows for the application of constant pressure to the manifold without damaging the nanoporous membrane. In some embodiments, the edges of the manifold may be bound to the top surface or outer edges of the biocompatible base substrate. While any sealing compound may be used, in some embodiments the sealing compound is an epoxy. In other embodiments, the pressure of the manifold on the at least one O-ring is sufficient to hold the nanoporous membrane in place. In some embodiments, one or more O-rings may be used. For example, a series of at least two, nested, concentric O-rings may be used. The nested, concentric O-rings may be placed in whatever position is useful. In one example, a first O-ring is sized and placed to surround the edges of the nanoporous membrane while a second, larger O-ring is sized and placed to surround the electrodes. In yet another embodiment, one or more O-rings may be positioned under the base substrate.

In some embodiments, the volume of sample required for effective detection of target analytes may be within a range from 20 microliters to 250 microliters, 25 microliters to 100 microliters, 50 microliters. A volume of sample containing target analytes of interest may be micropipetted into holes in the manifold. The sample then travels from the holes and onto the nanoporous membrane. The nanoporous membrane may wholly or partially trap the sample. In some embodiments, the majority of the sample is trapped in the nanoporous membrane while only trace seepage flows through the nanopores of the membrane to directly contact the electrode. In other embodiments, the sample is wholly held within the nanoporous membrane in direct contact with the electrodes.

In one embodiment, in order to functionalize a plain membrane sandwiched between the manifold and the sensor, a cross-linker is micropipetted into at least one of the group of openings on the biocompatible manifold to bind to the nanoporous membrane, initiating a functionalization of the nanoporous membrane. Such binding of the cross-linker to the membrane surface may be covalent, ionic or electrochemical. One or more detecting agent may be added to the nanoporous membrane through the openings in the biocompatible manifold to bind with the cross-linker in spaces in the nanoporous membrane. In a second example, a detecting agent may be a cross-reacting antibody, specific to the target analyte of interest that may specifically bind to the target analyte. Non-target analytes may negatively impact the sensitivity of the nanosensors, by binding non-specifically to reactive sites on the membrane or by non-specific binding to unbound cross-linkers. Thus, in further embodiments, a protein blocker may be added to one or more of the openings in the biocompatible manifold such that the protein blocker binds to voids and/or nonspecific sites (also known as reactive sites) on the nanoporous membrane. In additional embodiments, the protein blocker may bind to any unbound cross-linker. In the examples mentioned above, the protein used as a blocker may be any protein that does not bind specifically to one or more target analytes. Thus, in one example, the choice of protein blocker may be empirically determined for a given target analyte and other detection reagents used. In this way, the sensing performance of the nanosensor may be enhanced. In another embodiment, a nanoporous membrane may be functionalized by the addition of a target analyte of interest as the detecting agent (e.g. instead of an antibody as the detecting agent, as described in the earlier embodiment). Herein, a cross-linker is pipetted first into at least one of the group of openings on the biocompatible manifold so as to bind to the nanoporous membrane, thereby initiating nanoporous membrane functionalization. One or more target analytes may then be added to the nanoporous membrane through the openings in the biocompatible manifold to bind with the cross-linker in spaces in the nanoporous membrane. In one example, a purified sample of the target analyte may be added to functionalize the nanoporous membrane while in another example, a sample from the patient including one or more target analytes may be added. When the nanoporous membrane is functionalized with a purified sample of the target analyte, the antigen or biomarker may function as the detecting agent to cross-react with an antibody (specific to the antigen or biomarker of interest), present in a small volume of sample from patient. If antibodies are present in the sample, binding of the antibody to the analyte may be detected by a percentage change in impedance and vice versa. In the other example, when a sample including the target analyte (instead of purified antigen) is used to functionalize the nanoporous membrane, purified antibodies specific to the antigen may be added to detect the presence of the target analyte in the sample. If target analyte is present, binding of the antibody to the analyte may be detected by a percentage change in impedance and vice versa. A protein blocker may be added subsequently to the one or more of the openings in the biocompatible manifold to bind to voids and/or nonspecific sites (e.g. reactive sites) on the nanoporous membrane, thereby completing functionalization of the nanoporous membrane. In further embodiments, the nanoporous membrane may be functionalized prior to placing it between the manifold and the sensor.

Further provided is a method of determining the presence and/or concentration of one or more target analytes of interest in a sample using the composition described above. According to one example, a first sample is inserted through one or more of the openings in the biocompatible manifold covering a nanoporous membrane, functionalized as described above. A potentiostat is attached to the electric connector of the sensor and an alternating current is passed through the electrodes on the base substrate at one or more frequencies, wherein the frequencies may be optimized for a specific target analyte suspected of being present in the sample. In some embodiments, the impedance generated by each nanopore on the nanoporous membrane may be summed to produce a single signal at a specific frequency.

Optimal frequencies for each analyte of interest may be determined by any means generally used. In one example, a sample containing a known amount of a known analyte is micropipetted onto a functionalized nanoporous membrane mounted on the platform. The frequency at which the greatest change in impedance is measured in the sample containing known amounts of target analyte is determined to be the optimal frequency for the particular target analyte (calibration). The optimal frequency is then applied to the composition comprising a sample in which the presence and/or amount of the target analyte is unknown. The percentage change in impedance in a sample is then compared to a dose response curve for percentage change in impedance of a reference sample and the concentration of the target analyte in the sample is then determined. In some embodiments, reference frequencies are determined for a plurality of analytes and series of reference frequencies applied one at a time may be used to determine the amount and/or presence of a plurality of target analytes in a sample. In further embodiments, a combination of analytes may be used in a reference sample to determine the presence or absence of a plurality of analytes. For example, in the case of heart attack, both Troponin I and Troponin T biomarkers may be present in a sample obtained from a patient. Determining the concentration of both Troponin I and Troponin T in a sample may be accomplished using a reference sample containing both analytes. In some embodiments, diagnostic accuracy of biomarkers may be improved by testing for a combination of suspected target analytes in a sample whether the testing is for each analyte individually or for a combination of target analytes tested together. The presence of one or more target analytes in a sample including 1, 2, 3, 4, 5, 6, 7, 8, 9, 10, 11, 12 or more target analytes may be determined using the optimal frequency for the standard for each or a plurality of those target analytes. The amount of target analyte in the sample may be a large or small amount. In some embodiments, the amount may be between about attogram/ml to 1 milligram/ml, about 0.0001 picograms/ml to about 0.5 milligrams/ml, specifically about 0.009 picograms/ml or any fraction thereof, wherein about is ±5%. Sample sizes may vary from 1 µl to about 500 µl, about 25 µl to about 100 µl In some embodiments a sample may be about 50 µl, the volume of a drop of blood or water, wherein about is ±5%.

To the accomplishment of the foregoing and related ends, certain illustrative aspects of the system are described herein in connection with the following description and the attached drawings. The features, functions and advantages that have been discussed can be achieved independently in various embodiments of the present disclosure or may be combined in yet other embodiments, further details of which can be seen with reference to the following description and drawings. This summary is provided to introduce a selection of concepts in a simplified form that are elaborated upon in the Detailed Description. This summary is not intended to identify key features or essential features of any subject matter described herein.

BRIEF DESCRIPTION OF THE DRAWINGS

To easily identify the discussion of any particular element or act, the most significant digit or digits in a reference number refer to the figure number in which that element is first introduced.

DETAILED DESCRIPTION

Glossary

Figure 1:
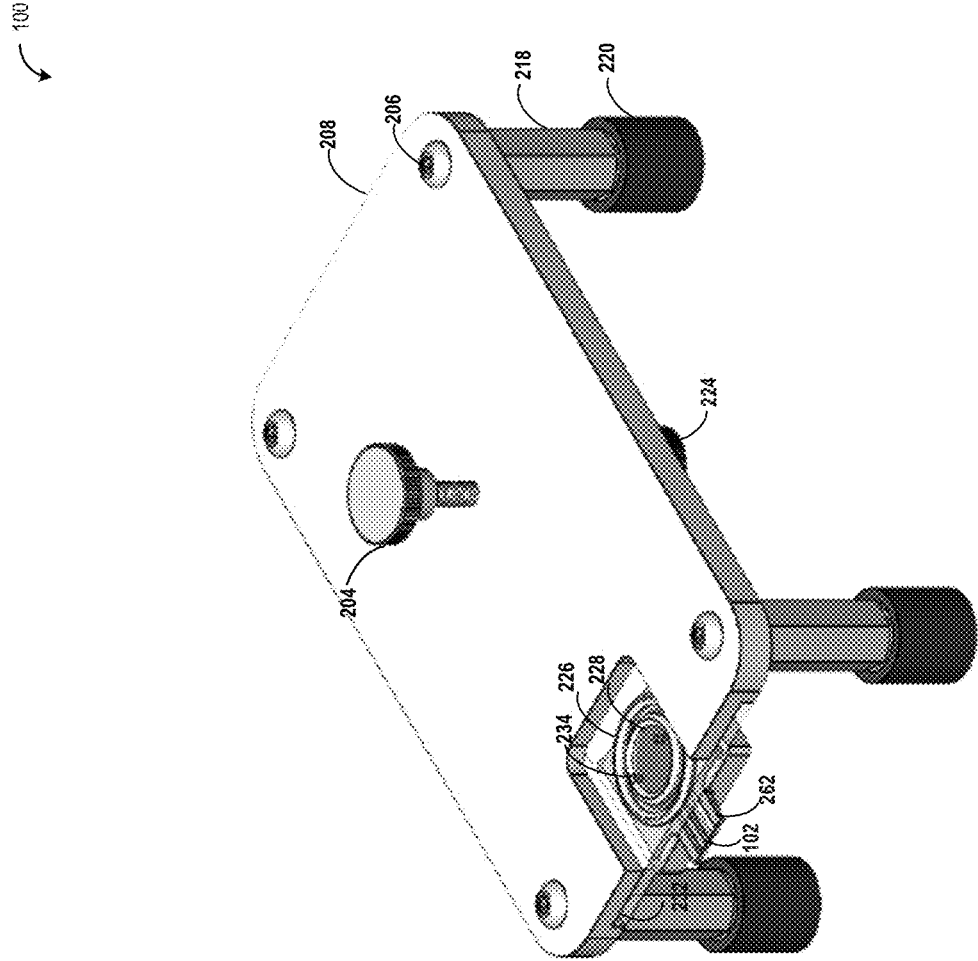
FIG. 1 illustrates a first embodiment of a platform for sealing the nanoporous membrane in a repeatable manner and including a nano-field electrical sensor for detection of target analytes in a sample.

"Mod" in this context refers to the magnitude of the impedance which acts like resistance, i.e. the ratio of the voltage difference amplitude to the current amplitude.

"Phase factor" in this context refers to the phase angle between the current and the voltage.

"Reactance" in this context refers to a form of opposition that electrical components exhibit to a change in current or voltage due to that element's inductance or capacitance.

Disclosed herein are methods and compositions for the detection and quantitative measurement of the presence of a target analyte in a sample based upon the electrical impedance of bound target analyte. Biomarkers may be detected alone or in combination in one or more bodily fluids for the prognosis, diagnosis, pharmacodynamic interactions, prediction, and monitoring of patients including identifying the presence of disease, the consequence of treatment, potential therapeutic effectiveness and disease progression respectively. In additional embodiments, such methods and compositions may be used to test environmental samples such as, but not limited to, water, air and soil for the presence of target analytes. Further disclosed is a testing platform for use with the composition for quantitative measurement of the presence of a target analyte. In some embodiments, the testing platform may be used to provide consistent, repeatable pressure on a nanoporous membrane on a base substrate. In this way, reproducibility of measurement and detection of target analytes of interest and performance of the membrane may be improved.

Biomarkers and other target analytes may be identified using a composition comprising a base substrate, one or more electrodes, a functionalized or plain nanoporous membrane, and a means for securing the base substrate, electrodes, and functionalized or plain nanoporous membrane together. In some embodiments, electrochemical impedance spectroscopy (EIS) may be used to detect biomarker or target analyte levels. In further embodiments, electrochemical impedance spectroscopy may be used to sum the field effect of all binding events that occur in the spaces on or within the nanoporous membranes. For example, a nanoporous membrane may be highly porous containing an estimated 764 million nano-spaces on a 24 mm$^2$ surface, each of which may generate a signal in response to a binding event. EIS sums all of the binding events in these spaces into one field to produce a single robust signal. In some embodiments, a small hand held electrochemical impedance scanning device may be used to test for a specific range of frequencies to provide prognostic, diagnostic, pharmacodynamic, predictive and progressive data. Such information may be transcribed to paper documentation or uploaded to an electronic medical record. In some embodiments, output values may be generated by the device itself. The output values in one example may be the presence or absence of the target analyte or analytes. In another example, the output may comprise a diagnosis of the disease condition based on detection of the target analyte (e.g. biomarker). In a further example, the output examples may indicate the amount of target analyte or analytes present. In other embodiments, output values may be generated using software in the cloud.

The compositions described herein have applications in a variety of fields including, but not limited to, differentiating between a normal state and a pathological state, smart sensor manufacturing; water and soil quality; food safety; drug detection in humans; and biological weapon detection. For example, in differentiating between a normal state and a pathological state, determinations may be made of the presence of biomarkers for sepsis, cardiovascular disease, bacteria, viruses, fungi, parasites, cancer and environmental contamination. In some embodiments, the composition described herein may be used in the identification of unknown biomarkers in a sample with a known exposure to an environmental contaminant or with a specific disease.

The composition described herein may be used alone or in combination with a testing platform as described herein. In additional embodiments, the composition may be used with point of care devices herein to provide data regarding biomarkers or target analytes within a shorter time frame than traditional laboratory analysis. In further embodiments, the composition may be used with the testing platform and a point of care device or the platform and care device may be combined into a single device. In some embodiments, the compositions described herein may be sensitive enough to be able to detect low concentrations of biomarkers or target analytes, such as concentrations between about an attogram/ml to 1 milligram/ml, about 0.0001 picograms/ml to about 0.5 milligrams/ml, specifically about 0.009 picograms/ml or any fraction thereof, wherein about is ±5%. In mammals, including humans, biomarkers may be identified from any bodily fluid including, but not limited to, saliva, blood, gingival crevicular fluid, serum, plasma, urine, nasal secretions, cerebrospinal fluid, pleural fluid, synovial fluid, peritoneal fluid, ascites, amniotic fluid, gastric fluid, ascites, lymph fluid, interstitial fluid, tissue homogenate, cell extracts, saliva, sputum, stool, physiological secretions, tears, mucus, sweat, milk, semen, seminal fluid, vaginal secretions, fluid from ulcers and other surface eruptions, blisters, abscesses, and extracts of tissues including biopsies of normal and suspect tissues or any other constituents of the body which may contain the target molecule of interest. Biomarker testing may be performed using samples collected using the same, different, or similar types of collection methods and the same, different, or similar types of bodily fluids to those used for prior collections and/or in comparison to the same or different electrochemical impedance spectroscopy or other testing methods.

In some embodiments, a target analyte may be obtained from an environmental sample such as water, soil, food, beverages, building products, bulk chemicals or reagents. Target analytes may include proteins, pathogens, heavy metal ions, small molecules, DNA, RNA, SNPs, microbes, agrochemicals, hydrocarbons, and the like.

The volume of a sample may be of any useful size. In some embodiments, the volume of sample (e.g. body fluids) required to detect target analytes may be a very small amount, for example between about 25 and 500 µl, about 25 to about 100 µl of sample. In one example, the amount in the sample may be about 50 µl, the volume of a droplet such as droplet of blood or water.

Biomarker levels in mammals such as humans can be affected by a number of factors including, but not limited to, gender, collection location, circadian rhythms, blood and environmental contamination, certain medications, and stability during storage. (Sbarouni E, Georgiadou P, Voudris V., Gender-specific differences in biomarkers responses to acute coronary syndromes and revascularization procedures. Biomarkers. 2011 September; 16(6):457-65. doi: 10.3109/

1354750X.2011.576431. Epub 2011 Aug. 19; Koh D S, Koh G C. The use of salivary biomarkers in occupational and environmental medicine. *Occupational and Environmental Medicine.* 2007; 64(3):202-210. doi:10.1136/oem.2006.026567.; Kugler K G, Hackl W O, Mueller L A, Fiegl H, Graber A, Pfeiffer R M. The impact of sample storage time on estimates of association in biomarker discovery studies. *Journal of Clinical Bioinformatics.* 2011; 1:9. doi: 10.1186/2043-9113-1-9.). Therefore, in some embodiments, the percentage change in impedance of a sample from an individual is compared with a dose response curve of percentage changes in impedance from a reference sample collected in the same or different manner from the same or different types of populations. In some embodiments, standard dose response curves measuring percentage changes in impedance may be from an age-matched population, a control population, a healthy age-matched control population, a gender-matched control population, a sample time matched population, or a combination thereof. In additional embodiments, sample analysis may be compared to standard levels taken at the same time of day. In further embodiments, sample analysis may be compared to standard levels of individuals with the same or similar genetic profiles. In additional embodiments, sample analysis may compare the percentage change in impedance levels in the same individual at different time points during a treatment protocol.

The sensitivity and reproducibility of the composition relies on constant testing conditions. For example, variations in volume between a reference sample and test sample may produce inaccurate results and the presence of contaminants may further confound the results. In another example, the method of application of the electrodes to the base substrate may affect the sensitivity of the composition. While traditional etching and printing methods of putting the electrodes on the base substrate may be used, in testing small samples with very small amounts of the target analyte, such methods of applying electrodes to the base substrate may generate false negatives. Similarly, the use of printed circuit board may provide a surface that introduces contaminants to the sample or to the electrodes, affecting the accuracy of the results. While not wishing to be bound, it is currently theorized that these contaminants change the porosity of the surface of the base substrate. It is also theorized that these contaminants may interfere in the proper adhering of the electrodes to the base substrate. Therefore, in some embodiments, vapor deposition of the material used to form the electrodes is used.

The base substrate may comprise any useful material that does not introduce contaminants into the electrodes during the electrode application process. For example, exemplary base substrates may be biocompatible, may support electrodes and/or have insulating properties. Exemplary materials include, but are not limited to, paper, nitrocellulose, ceramics, plastics, metals, alumina and the like.

In one embodiment, there may be a plurality of holes through the base substrate around the working electrode. Such holes may have any cross section desired including, but not limited to, cylindrical, elliptical, hexagonal, slit, octagonal, rhomboid, or any other desired shape. In one example, the plurality of holes may be arranged equidistant from each other and be positioned around the circumference of the gold working electrode. In some embodiments, the holes may allow for flow of the sample analyte, optimizing the exchange that occurs in the nanoporous membrane.

While any nanoporous membrane having a plurality of nano-spaces may be used, in some embodiments the nanoporous membrane is an electrospun membrane. The electrospun membrane may be of any useful material, weight, air permeability, tensile strength, elongation, pore size and bubble size. The electrospun membrane may be of any suitable material including, but not limited to, polyurethane, poly(vinylidene fluoride), nylon or polyethersulfone, and combinations of one or more of these or other suitable materials.

For example, the electrospun membrane may be about 2.00 g/m$^2$ in weight with an air permeability of 8.80 l/m$^2$/sec at 125 Pa. In some examples, it may have a CD tensile strength of about 1.60 kgf/in and a MD tensile strength of about 7.00%. In other embodiments, it may have a cd elongation of 17.0% and a MD elongation of 19.0%. In additional embodiments, a nylon electrospun membrane may have a combination of all of these properties with a mean pore size of about 0.21 μm and a maximum bubble pore size of 0.24 μm.

The manifold may be of any biocompatible material generally used. In some embodiments, it is metallic. In other embodiments, it is a polymer. Such manifolds may be opaque or transparent. In one example, the manifold has insulative properties.

FIG. 1 depicts a platform 100 that may be used for the detection of target analytes. The platform may include a base plate 208 and a platen (platen 216 shown in FIG. 2) with a manifold 232 affixed to a first recess 250 on the bottom surface 252 of the base plate 208. In some embodiments, the combination of the base plate 208, platen 216, and manifold 232 may together make up a reaction space in which binding to the nanoporous membrane in place over the nano-field electrical sensor 102 can occur. In one example, the base plate may be mounted on top of the platen and the nano-field electrical sensor may be positioned on the platen. The base plate and the platen may be any suitable substrate of any suitable shape, size or material including, but not limited to, aluminum, stainless steel, polytetrafluoroethylene, high carbon steel, viton fluropolymer and combinations thereof as appropriate for one or more parts of the base plate and the platen. In some embodiments, the base plate 208 may be shaped with a first cutout 236 on a first end 240. In an additional embodiment, the base plate 208 may have a recess 250 on a bottom surface where the manifold 232 may be attached. The manifold may be affixed in the recess 250 by any means generally used. In some embodiments, the manifold is mechanically affixed to the recess, for example through the use of screws 270 or other fasteners. The base plate may have legs such as the hex standoffs 218. In some embodiments, the legs of the base plate may further comprise bumpers 220 which may, in some instances, stabilize the testing platform and insulate it from vibrations.

The platen may have a receptacle 238 at a first end 258 with a second cutout 254, wherein the receptacle is designed to hold the sensor nanoporous membrane combination and the second cutout 254 is designed to hold an electrical connector of the sensor where the electrical connector 262 is designed to attach to a potentiostat to measure electrical impedance. The distance and or compression between the base plate and the platen is controlled in some embodiments by a thumb screw 204 and a thumb nut 224.

The nano-field electrical sensor 102 may comprise any base substrate 104 that is capable of supporting a plurality of electrodes. For example, exemplary base substrates may be biocompatible, may support electrodes, and/or have insulating properties. Exemplary materials include, but are not limited to, paper, nitrocellulose, ceramics, plastics, metals, alumina and the like. In one example, a suitable base substrate may be ceramic such as alumina ($AlO_3$). Electrodes may be placed or deposited on a first surface 256 of the base substrate 104. In some embodiments, the electrodes may be of the same noble metal. In other embodiments, the electrodes may be of different noble metals. For example, a working and counter electrode may be gold, while the reference electrode may be silver. In some embodiments, the electrodes may be placed on an alumina base substrate. In additional embodiments, electrodes may be printed on a base using any appropriate conductive material such as a metal or metal oxide nanoinfused conductive ink. In yet other embodiments, electrode material may be placed on the surface of the substrate by chemical vapor deposition. Each electrode may be deposited on the base substrate by the same or different methods. In one example, a layer of titanium is placed over the base substrate 104 and the electrodes are placed on top of the titanium layer.

Figure 2:
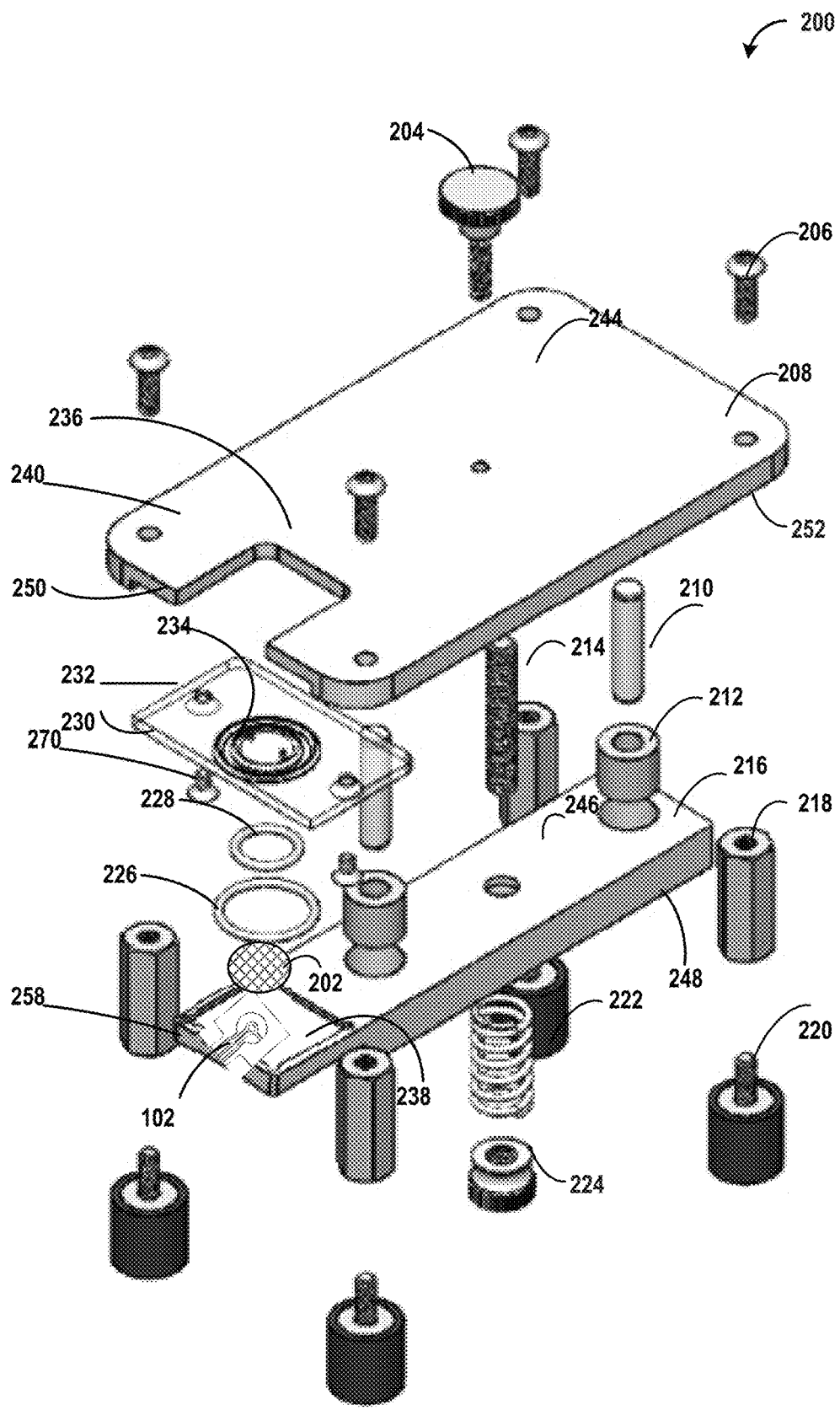
FIG. 2 is an exploded view showing various parts of the platform used in detection of target analytes in accordance with the embodiment of FIG. 1.
Figure 3:
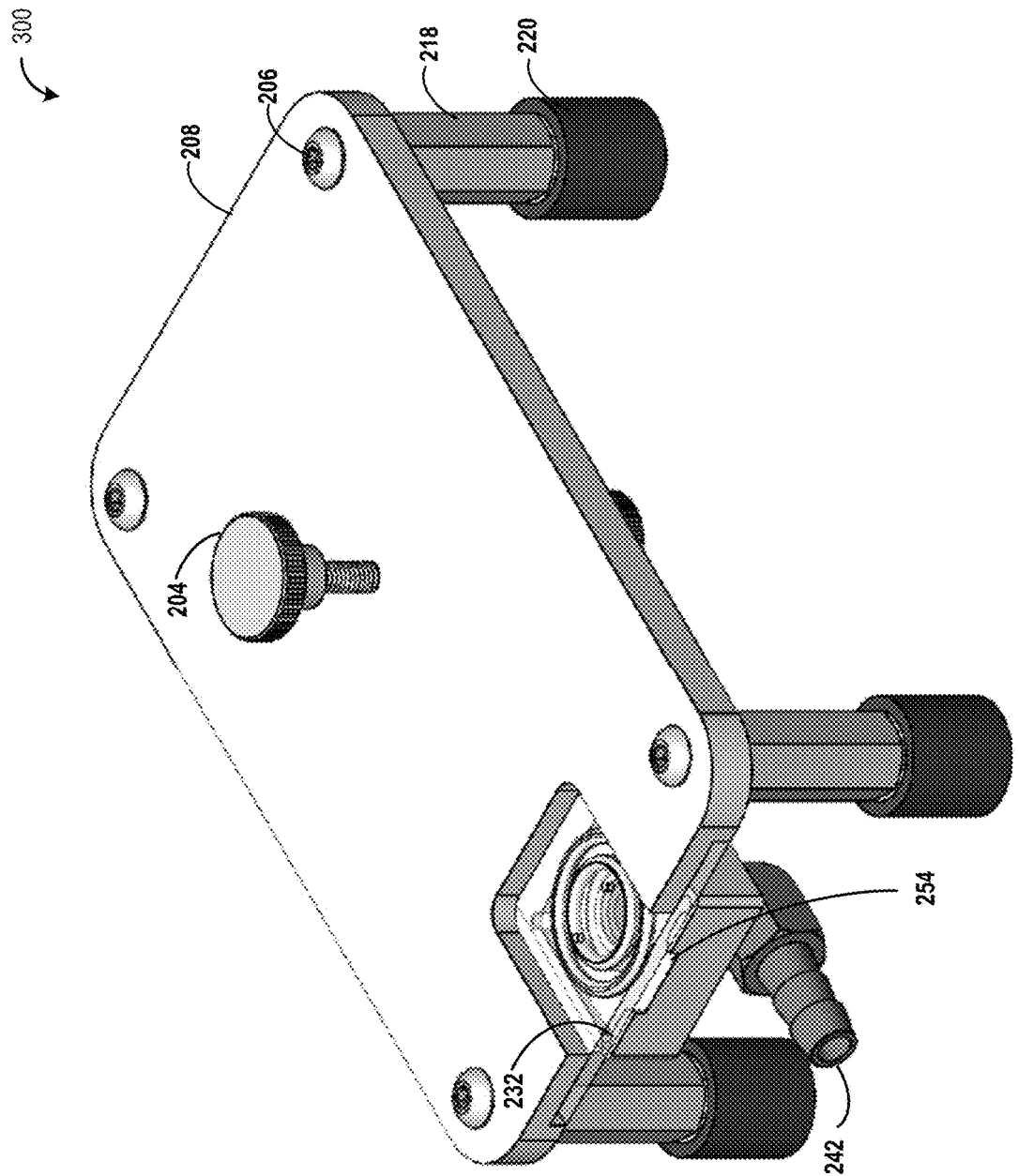
FIG. 3 illustrates a second embodiment of a platform for sealing the nanoporous membrane in a repeatable manner and including a nano-field electrical sensor for detection of target analytes in a sample.
Figure 4:
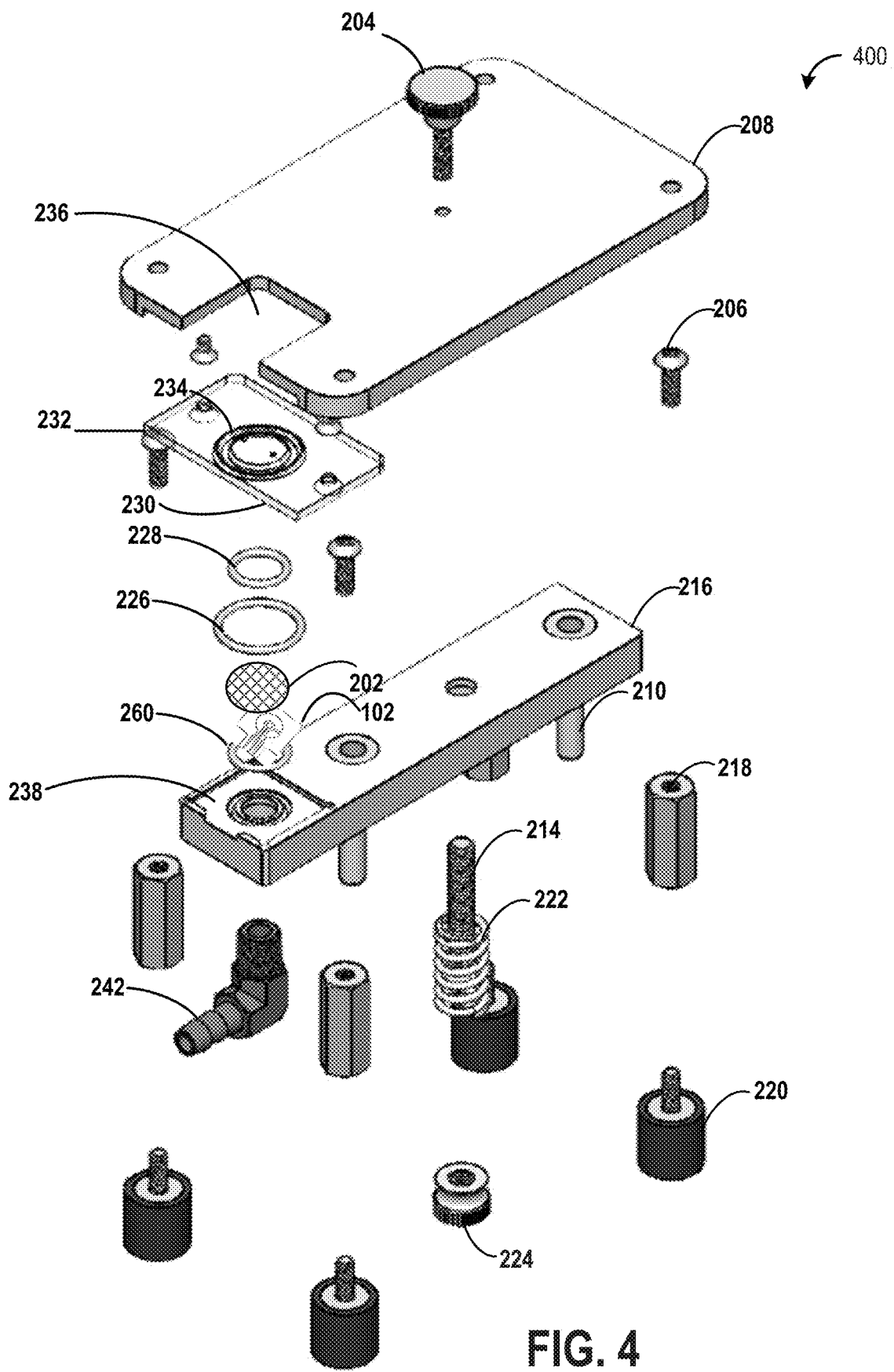
FIG. 4 is an exploded view showing various parts of the platform used in detection of target analytes in accordance with the embodiment of FIG. 3.

FIG. 2 is a schematic 200 showing various parts of the testing platform used for detection of target analytes. As described above, the composition for detecting analytes in a sample may include a nanoporous membrane 202 placed over one or more sensor electrodes on a base substrate 104 and a manifold 232 holding the nanoporous membrane 202 in place on the sensor electrodes. In some embodiments, the manifold 232 may be held in place by a testing platform comprising a base plate 208 and a platen 216 as shown in FIG. 1. The manifold 232 may fit into a recess 250 at a first end 240 of the base plate 208. In one embodiment, the composition may further comprise at least a first O-ring 228 and a second O-ring 226. The O-rings may be two concentric O-rings, wherein O-ring 228 may be smaller than and nest within O-ring 226. Further, the two O-rings may or may not be coplanar. The larger O-ring 226 may hold the nanoporous membrane in place over the nano-field electrical sensor 102 while the smaller O-ring may be used to contain any liquids inserted through the manifold onto the nanoporous membrane. A clear acrylic manifold 232 or other biocompatible manifold such as a metal manifold may be mounted over the smaller O-ring such that the openings on the manifold (e.g. opening 234) through which the one or more target analytes may be added may be within a well within the periphery of the smaller O-ring 228. In one example, the O-rings may further be made of fluoroelastomers and may further be resistant to a wide range of chemicals. The set of O-rings thus positioned may function to dynamically seal the nanoporous membrane to the sensor electrodes and may further provide a constant pressure seal to maintain consistency in sample volumes being tested. For example, the well may hold a fixed sample volume once the manifold has been mounted over the O-ring and clamped down. In some embodiments the O-rings are fastened to a bottom surface of the manifold 230. By maintaining constant pressure, the sample size/volume may be kept constant when testing different target analytes, thereby increasing the efficiency and reproducibility of the system. In one embodiment, the sample containing the target analyte may pass from the well through the membrane by gravity. In a second embodiment, one or more optional O-rings such as O-ring 260 may be placed below the base substrate as shown in FIG. 4. When placed below the nanoporous membrane, the composition comprising a third O-ring 260 may further be used in combination with a vacuum hose 242 as depicted in FIGS. 3 and 4. In this configuration, the vacuum hose 242 may connected to a source of vacuum (e.g. vacuum pump, not shown) so as to use suction to draw the sample containing analytes introduced via manifold openings to a well and then through the membrane. In one example, the use of a vacuum hose may help speed the detection reaction, especially when nanoporous membranes with relatively small pore sizes are used. The use of an O-ring below the membrane may help to prevent backflow of liquids and maintaining a uniform shape of the nanoporous membrane when suctioned under vacuum.

The base plate 208 of the manifold may be clamped to the platen 216 to immobilize the nanoporous membrane 202 over the nano-field electric sensor 102 while the well, limited by the O-rings may allow for reproducible sample sizes.

In between the base plate and the platen, one or more bearings may be provided such as bearing 212. The bearing 212 may be made of any suitable material. In one example, the bearing 212 may be made of Teflon™. These bearings may resist high temperatures and a range of chemicals, and may further decrease the resistance to the movement of the base plate. The platform of FIG. 2 may further be clamped by one or more button head screws 206 and steel dowels 210. In one embodiment, four screws spaced apart at the periphery of the base plate and two steel dowels to be used as a fixture with the Teflon™ bearings may be employed to ensure an efficient seal.

The base plate may be on four legs. In some embodiments, the legs may include one or more hex standoffs 218 that may function to provide the platform including the base plate and the attached platen with a firm grip to the surface on which it is placed. In addition, one or more bumpers 220 with built-in studs and steel base plates may reinforce the platform and may additionally permit cushioning and vibration damping. A thumb screw 204 is attached to a threaded rod 214. The threaded rod 214 may pass through a hole in the base plate and a hole in the platen, passing through the first surface 244 of the base plate, out the bottom or second surface of the base plate 252, through the first surface 246 of the platen and out the second surface 248 of the platen. A compression spring 222 in contact with a second surface 248 of the platen may surround the threaded rod 214, which is capped by a thumb nut 224. In some embodiments, the compression spring may withstand a pressure of 1-2 lbs.

Loosening the thumb screw 204 may lower the platen, allowing a sensor and nanoporous membrane over the electrodes of the sensor to be inserted into the receptacle 238 at the first end 258 of the platen. Tightening the thumb screw 204 will raise the platen against the manifold and the base plate such that constant pressure is applied to the O-rings 226 and 228 resting on top of the nanoporous membrane 202. Constant pressure will also be applied against additional O-rings such as against a third O-ring below the base substrate shown in FIG. 4.

The top of the platform may include alumina base plate 208 that may clamp down on manifold 232, the nested set of O-rings 226 and 228, the nanoporous membrane 202, the nano-field electrical sensor 102 and the platen 216 in the order respectively. In one embodiment shown in FIG. 2, the baseplate may have a rectangular shape with a first cutout 236. The base plate may be secured to legs such as hex standoffs 218 using one or more button head screws 206 that may have nylon patches to resist loosening due to vibrations. Additionally, a large thumb screw 204 may be positioned centrally over the base plate that may serve to seal the manifold (seal the baseplate with the platen), with the target analyte sensing system in between the base plate and platen, when tightened as shown in FIG. 1. When the thumb screw is loosened, it may raise the base plate upward, allowing access to the target analyte sensing system as shown in FIG. 2.

The nano-field electrical sensor 102 in the platform of FIG. 1 may further be connected to an EIS potentiostat device for performing electrochemical impedance spectroscopy configured to measure impedance at one or more frequencies for a specific target analyte.

The nanoporous membrane may be functionalized before or after manifold sealing through the addition of one or more chemical linkers through the plurality of openings in the manifold to the well including, but not limited to, cross-linking agents including compounds containing hydrazone, disulfides, amides, peptides, thioether bonds and/or amine-reactive cross linkers such as, but not limited to, dithiobis succinimidyl propionate, di succinimidyl suberate, 3,3'-dithiobis(sulfosuccinimidylpropionate) (DTSSP), bis(sulfosuccinimidyl)suberate ($BS^3$), disuccinimidyl tartarate (DST), disulfosuccinimidyl tartarate (sulfo-DST), bis [2-(succinimidyloxycarbonyl oxy)ethyl]sulfone BSOCOES, bis[2-(sulfosuccinimidyl oxycarbonyl oxy)ethyl]sulfone (sulfo-BSOCOES), ethyleneglycolbis (succinimidyl succinate) (EGS), ethylene glycolbis(sulfosuccinimi dylsuccinate) (sulfo-EGS), dicuccinimidyl gluarate (DSG), N,N'-disuccinimidyl carbonate (DSC), and bisNHS(PEG)n; homofuncitonal imidoesters such as dimethyl adipimidate (DMA), dimethyl pimelimidate (DMP), dimethyl suberimidate (DMS), dimethyl 3,3-dithobispropionimidate(DTBP); heterofuncitonal crosslinkers including, but not limited to, NHS-hydrazine moiety (SANH), NHS-adldyde moiety (SFB) etc. In the trifunctional crosslinkers, there are 4-azido-2-nitrophenyl-biocytin-4-nitrophenyl ester (ABNP), and sulfosuccinimidyl-2-[6-(biotinamido)-2-(p-azidobenzamido) hexanoamido] ethyl-1, 39-dithopropionate (sulfo SBED).

Figure 5A:
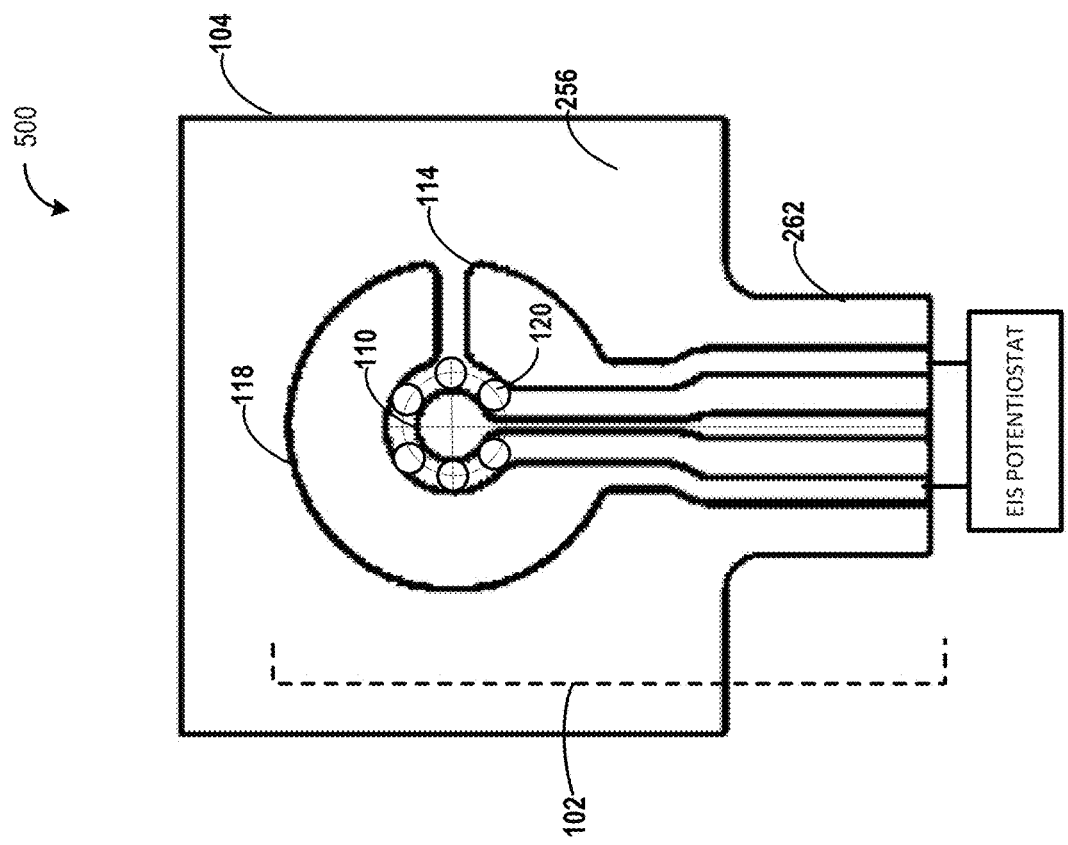
FIG. 5A is a schematic of the nano-field electrical sensor showing a gold working electrode, a gold counter electrode and a silver reference electrode on a ceramic base

The nano-field sensor 102 may comprise one or more electrodes, such as a working electrode, a counter electrode and a reference electrode as illustrated in FIGS. 5A and B. In one embodiment, the working electrode and the counter electrode may be made of gold while the reference electrode may be made of silver. Silver electrodes may be non-polarizing and offer zero impedances (e.g. allows current to pass through the interface between the electrolyte and the electrode). The use of gold and silver noble metals for use as electrodes may result in decreasing contaminants that may inhibit ligand binding. In some embodiments, the sensitivity of the impedance measurements may be affected by potential contaminants in the gold and/or silver used to form the electrodes. In some examples, the gold and silver have a purity of greater than 90%, greater than 95%, 99% or greater. Further, such electrodes may be robust and tolerate moderately high temperature. In other embodiments, any appropriate conductive material such as a metal or metal oxide nanoinfused conductive ink may be used as an electrode. Sensitivity of the sensor in the composition may also be impacted by the surface area and spacing between the electrodes. In some embodiments, the surface area of the counter electrode is about 65 $mm^2$ to about 75 $mm^2$ or any fraction therefor. In one embodiment, the surface area is about 72 $mm^2$. In another example, the surface area of the counter electrode is about 71.6 $mm^2$, where "about" refers to +/−10%, +/−5%, +/−1% or any fraction thereof. The surface area of the working electrode may be about 2 to about 7 $mm^2$ or any fraction thereof. In some embodiments, the surface area of the working electrode may be about 6 $mm^2$ where "about" refers to +/−10%, +/−5%, +/−1%. The surface area of the reference electrode is about 15 to about 20 $mm^2$ or any fraction thereof. In some embodiments, the surface area may be about 18.7 $mm^2$ where "about" refers to +/−10%, +/−5%, +/−1%.

Figure 5B:
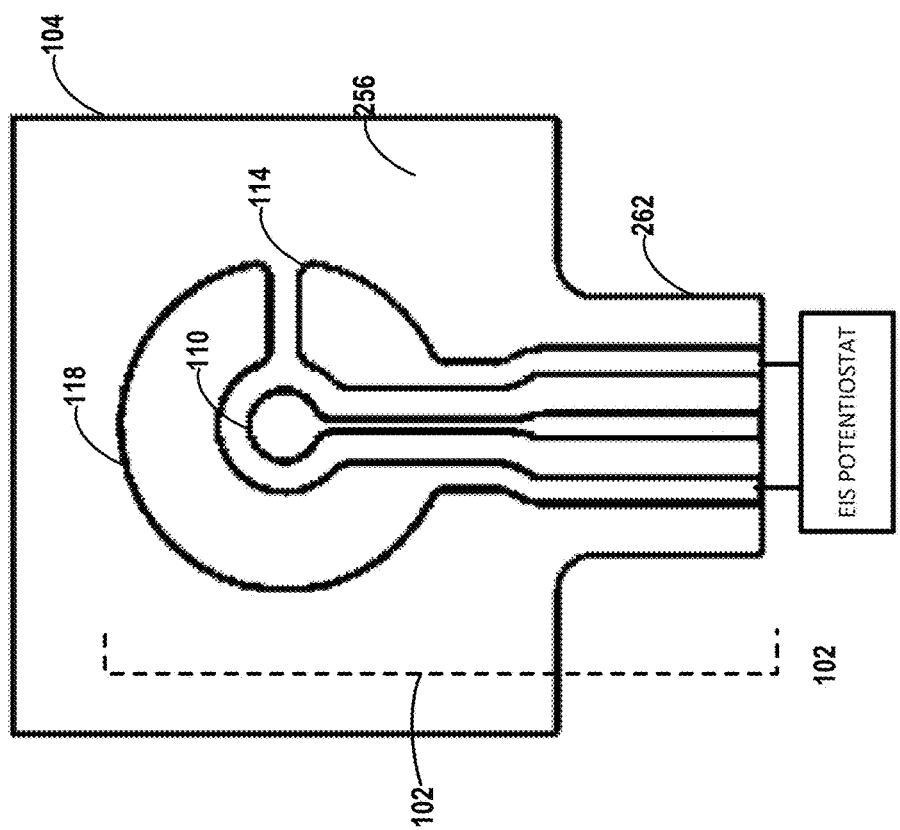
FIG. 5B is a schematic of a nano-field electrical sensor showing a gold working electrode, a gold counter electrode and a silver reference on a ceramic base with perforations on the ceramic base.

While of any suitable shape and design, in some embodiments the electrode pattern may be devoid of 90° angles, producing a circular design in solid concentric circles as shown as shown by illustration 500 in FIG. 5A. In another example, the electrode pattern may produce branched interlocking concentric circles. In one embodiment, a plurality of holes 120 may be present on the base substrate between the reference and working electrodes as shown in FIG. 5B. Such holes may have any cross section desired including, but not limited to, cylindrical, elliptical, hexagonal, slit, octagonal, rhomboid, or any other desired shape. As shown in FIG. 5B, the plurality of holes may be arranged equidistant from each other and be positioned around the circumference of the circularly designed gold counter electrode. In one example, the holes 120 on the base substrate 104 of the nano-field electrical sensor 102 may be flow holes. When envisioned in combination with the second embodiment of the platform shown in FIGS. 3 and 4, where one or more O-rings may be positioned above the nanoporous membrane 202 and/or below the base substrate 104, the target analyte containing sample may be suctioned through the nanopores on the membrane, and further through the base substrate via the holes. By increasing the flow of sample via the membrane, target analyte detection may be accelerated.

Figure 15:
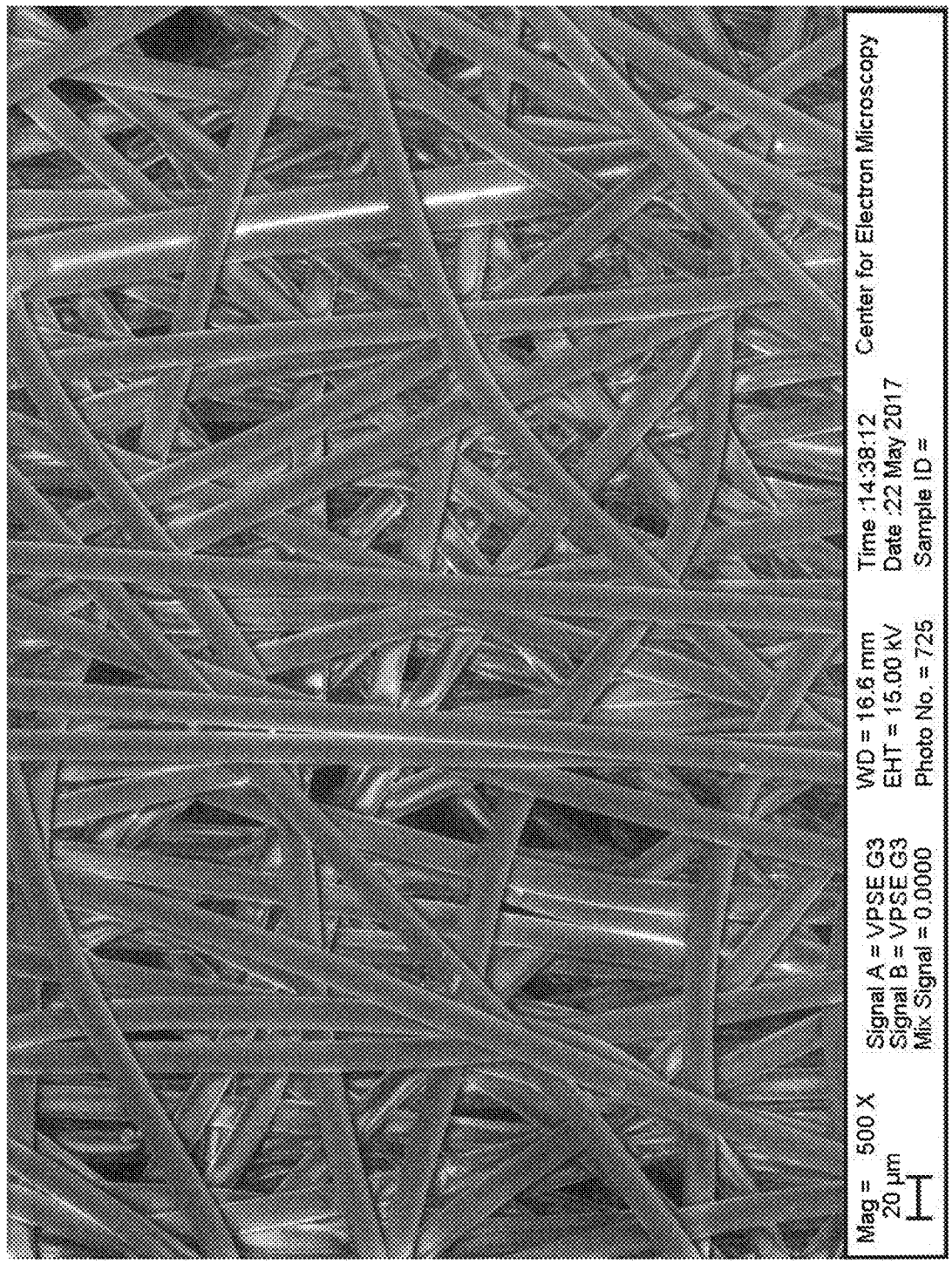
FIG. 15 is a scanning electron micrograph of the non-functionalized nanoporous membrane displaying nanopores.

A nanoporous membrane 202 may be placed on the nano-field electrical sensor 102. Exemplary nanoporous membranes may comprise any suitable membrane. In some embodiments, the nanoporous membrane is thin, flexible and shapeable. The nanoporous membrane may be extremely porous such as shown in the scanning electron microscope image of FIG. 15. Nanoporous membranes may be polyamides such as, but not limited to, aliphatic polyamides such as, but not limited to, nylon; aromatic polyamides such as, but not limited to 2-methacryloyloxyethyl phosphorylcholine. In further embodiments, nanoporous membranes may be porous nanocrystalline silicon, a mixed matrix nanoporous membrane, or an electrospun nanofiber membrane. The porosity of the nanoporous membrane may be of any degree required, in some embodiments, a nanoporous membrane may have 10%, 20%, 30%, 40%, 45%, 50%, 55% or 60% porosity. In targeting a particular analyte with a defined size, nanoporous membranes with different porosity or different shapes of pores may be selected as needed to increase the sensitivity of detection. While the percent porosity will influence the size and number of pores, in some embodiments, the diameter of one or more pores may be between about 1 nm to about 3000 nm or any fraction thereof, such as about 1, 5, 10, 15, 20, 25, 30, 35, 40, 45, 50, 100, 200, 300, 400, 500, 600, 750, 1000, 1250, 1500, 1750, 2000, 2250, 2500, 2760 nm in diameter or any fraction thereof. For example, a nylon nanoporous membrane with 45-50% porosity and a 200 nm pore size has an estimated 746 million spaces available for binding. In some embodiments, the diameter of the nanometer pores in a nanoporous membrane may be the same size (uniform). In other embodiments, the diameter of the nanometer pores in a nanoporous membrane may be different, wherein one or more nanopores may be the same or different from one or more additional nanopores. The nanopores may be of any useful cross section, including, but not limited to, cylindrical, elliptical, hexagonal, slit, octagonal, rhomboid, or any other regular or irregular cross-shape. Such spaces within the nanoporous membrane may be used to simultaneously identify single or multiple target analytes.

Means for securing the base substrate, sensor electrodes, and nanoporous membrane together may be any manifold suitable of being sealed onto the base plate to hold the nanoporous membrane in place. For example, in some embodiments, the manifold may be attached to the base substrate using a sealant such as, but not limited to, an epoxy. In some embodiments, in addition to or instead of using epoxy, screws may be used to clamp down on the composition. In some embodiments, the entire manifold may be biocompatible. In other embodiments, the manifold may be a biocompatible material with insulating properties such as, but not limited to, alumina. In some embodiments, the manifold may be alumina or other metallic manifold. In some embodiments, a manifold made of clear acrylic may be mounted over the nanoporous membrane such that the manifold may allow for viewing of one or more target analytes through the addition of a sample via a plurality of openings in the manifold including 1, 2, 3, 4, 5, 6, 7, 8 or more openings. In some embodiments, the opening may be circular holes such as shown in FIG. 2, though the cross-section of such an opening may be any shape useful including a rhombus, triangle, elliptical, pentagonal, hexagonal, octagonal shape or the like. Each opening may be the same or different from other openings in the manifold. The spacing between each opening may be about 180°, though any fraction of the perimeter of the manifold may be used.

Figure 6:
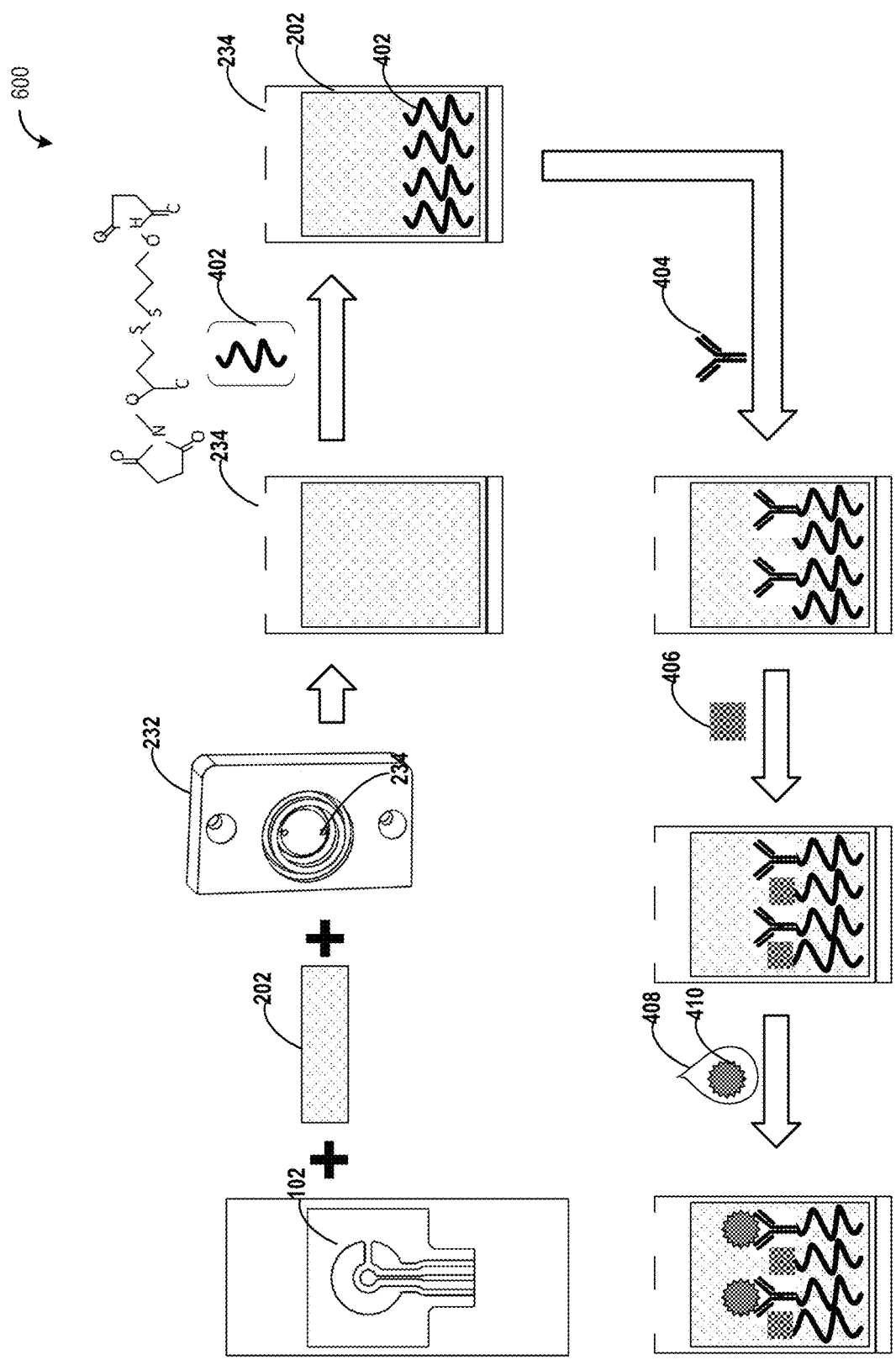
FIG. 6 illustrates a first embodiment of a cartoon of construction, functionalization and capture of antigens in target analyte using a nano-field electrical sensor.

Nanoporous membranes may be further functionalized by detecting agents including, but not limited to, antibodies, antigens, nucleic acids (DNA, RNA, aptamers, oligomers), chemical reactions, and oxidation reactions. FIG. 6 illustrates a cartoon 400 showing construction, functionalization and capture of an antigen using a nano-field electrical sensor. The platform of FIG. 2 may need to be assembled as shown in FIG. 6 before membrane functionalization and addition of target analyte sample. In one embodiment, ceramic base containing the nanosensor electrodes may be overlayed with nanoporous membrane 202. The nanoporous membrane may be held in place over the sensor with O-rings (shown before) and further with the manifold 232, including opening 234 for the addition of the sample. Membrane functionalization in some embodiments, may involve applying a series of agents such as, but not limited to, crosslinking agents such as dithiobis succinimidyl propionate (DTSP) 402, a detecting agent 404, followed by a protein blocker 406 as shown in FIG. 6 to bind all unbound spaces and/or to bind free DTSP to decrease non-specific binding of antigens. When an electric field is applied, the binding of the biomarker or target analyte (e.g. antigen 408 shown in FIG. 6) to its detecting agent 404 changes the impedance which is measured by the EIS and may be summed across all of the nanospaces in the nanoporous membrane to produce a signal that is currently theorized to be correlated to the concentration of the biomarker or target analyte in the sample.

Figure 7:
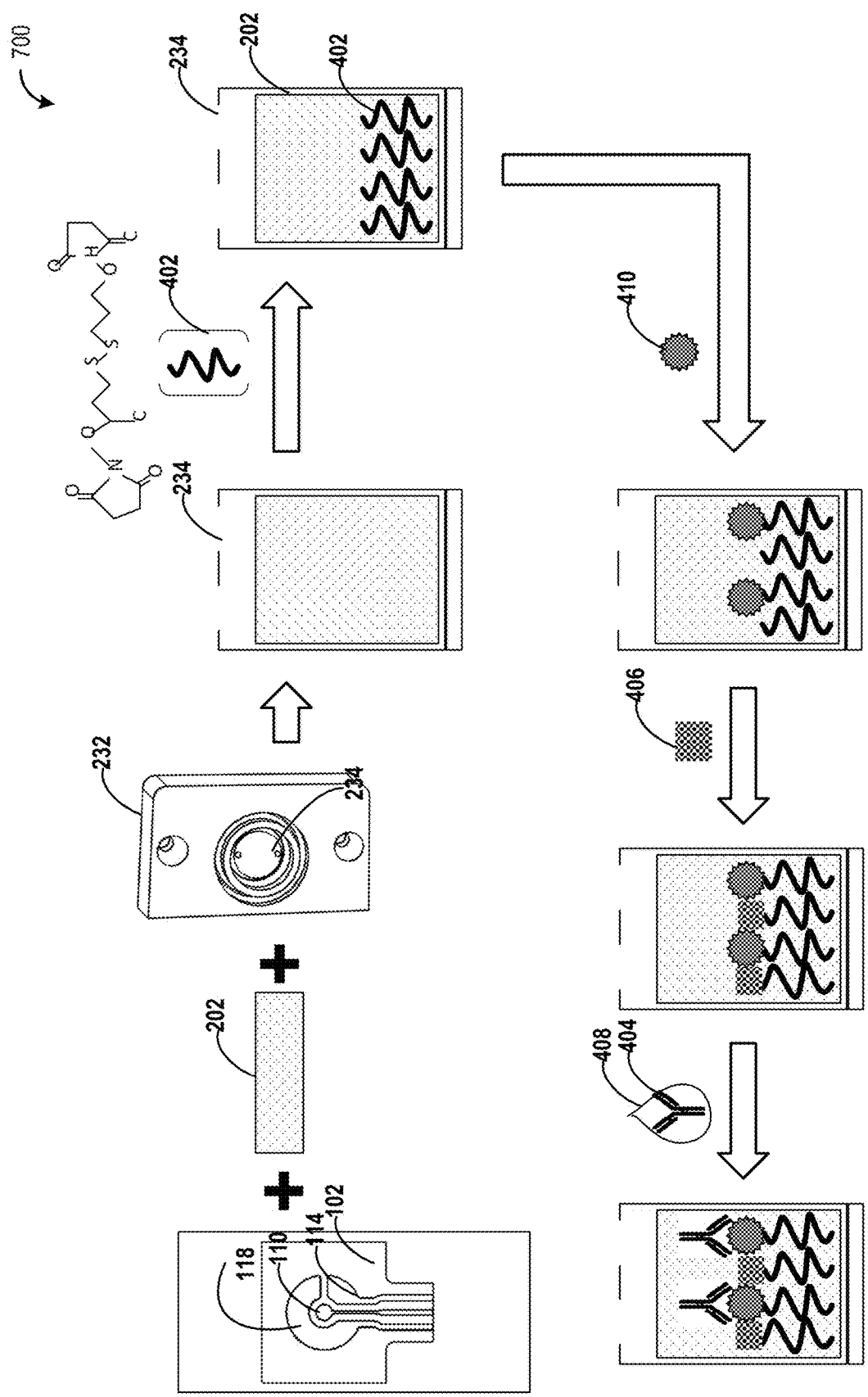
FIG. 7 illustrates a second embodiment of a cartoon of construction, functionalization and capture of antibodies in target analyte using the nano-field electrical sensor.

As shown in FIG. 6, a nanoporous membrane 202 is placed on the nano-field electrical sensor 102, over the gold working electrode 110, the gold counter electrode 118, and silver reference electrode 114 (See FIG. 7). An acrylic manifold 232 is then bound over the nanoporous membrane 202, holding it in place on the nano-field electrical sensor 102. A crosslinking agent 402 such as the amine-reactive crosslinker DTSP as shown in FIG. 6 is then added through an opening 234 to the well. The crosslinking agent may bind to the nanoporous membrane as described before. A detecting agent 404 is then added through opening to be combined with the nanoporous membrane 202, and crosslinking agent 402. After the addition of the detecting agent 404, a protein blocker 406 is added to bind to the unused crosslinking agent 402 decreasing any voids left by the crosslinking agent 402 as well as to any unbound crosslinking agent 402. An amount of the sample 408 is then added through the manifold opening 234 and the target analyte 410 is bound by the detecting agent 404. When an electric field is applied across the membrane, the binding of the target analyte (e.g. biomarker or antigen of interest) to the detecting agent (e.g. antibody) leads to an impedance as measured by the EIS potentiostat.

For example, a functionalized electrospun nanoporous membrane 202 may be placed on a nano-field electrical sensor 102 comprising a biocompatible base substrate 104 having a top surface 256 onto which at least two electrodes (110 and 114) in a capacitive relationship have been placed. The nanoporous membrane 202 and the sensor are inserted into a receptacle 238 (as shown in FIG. 2 and FIG. 4), with the portion of the sensor used to attach to a potentistat extending through a second cutout in the receptacle 238 at the first end of the platen 216. A manifold 232 is affixed to the first recess 250 at a first end of the base plate. The platen 216 and the base plate 208 may be arranged coplanar in a horizontal plane with the bottom surface 252 of the base plate and the top surface 246 of the platen are in contact and the manifold 232 at the first end of the base plate 208 covers the nanoporous membrane 202 in the receptacle 238 at a first end 258 of the platen 216. The combination of the manifold, base plate and receptacle 238 of the platen 216 serve to form a reaction space for the nanoporous membrane. A sample 408 suspected of containing the analyte of interest 410, is micropipetted through a hole 234 in the manifold 232 and into a well A potentiostat (not shown) is attached to the portion of the sensor extending through the second cutout 254 (FIG. 3) in the receptacle 238 of the platen 216. An electric current is sent through the electrodes on the sensor and the impedance of the sample is measured. The percentage change in impendence of the sample is correlated into a concentration of the analyte of interest 410 by comparing the percentage change in impedance of the sample with the percentage change in impedance of a prior reference sample such as in a dose response curve.

As shown in FIG. 7, in some embodiments, a nanoporous membrane 202 is placed on the base substrate 104 of the nano-field electrical sensor 102, over the gold working electrode 110, the gold counter electrode 118, and silver reference electrode 114. An acrylic manifold 232 is then bound over the nanoporous membrane 202, holding it in place on the base substrate 104 of the nano-field electrical sensor 102. A crosslinking agent 402 such as the amine-reactive crosslinker DTSP as shown in FIG. 7 is then added through an opening 234 in the manifold 232. The crosslinking agent may bind to the nanoporous membrane as described before. A target analyte 410 is then added through the opening 234 and binds with the crosslinking agent 402 on the nanoporous membrane 202. A protein blocker 406 is then added to bind to the unused crosslinking agent 402 decreasing any voids left by the crosslinking agent 402 as well as to any unbound crosslinking agent 402. An amount of the sample 408 is then added through the manifold opening 234 and the target analyte 410 is bound by the detecting agent 404. As shown in FIG. 7, the detecting agent 404 may be an antibody specific to the target analyte 410, such that when the sample is added to the functionalized nanoporous membrane, binding of the antigen to the antibody (if present in the patient sample) may be detected. When an electric field is applied across the membrane, the binding of the target analyte (e.g. biomarker or antigen of interest) to the detecting agent (e.g. antibody) leads to a change in impedance compared to control, as measured by the EIS.

In some embodiments, the functionalized nanoporous membranes may have a detection limit of about attogram/ml to 1 milligram/ml, about 0.0001 picograms/ml to about 0.5 milligrams/ml, specifically about 0.009 picograms/ml or any fraction thereof, wherein about is ±5%. In additional embodiments, the maximum dynamic range may be up to about 1 gm/ml or a fraction thereof. As shown in the Examples below, biological samples show a frequency dependent behavior to an applied alternating electrical signal. When using alternating electrical excitation, the biological samples have a bioelectrical impedance that depends on the biological sample and the frequency of the applied electrical current. Such quantities may be represented by real part of impedance, the resistance and the reactance (imaginary part of impedance). Bioelectrical impedance spectroscopy estimates the real imaginary part of the electrical impedance over a wide frequency range where impedance is calculated as:

$$Z = Z\text{real} + Z\ im.o,g = |Z|ei0$$

The Mod was calculated using the following equation:

$$|Z| = \sqrt{Z_{real}^2 + Z_{imag}^2}$$

The phase factor between the current and the voltage can be represented as $<I> = \tan{-1}(Z\text{real}/Z\ \text{imag})$.

Further provided is a method of determining the presence and/or concentration of one or more target analytes of interest in a sample using the composition described above wherein a first sample is inserted through one or more of the openings in the biocompatible metallic manifold covering a functionalized nanoporous membrane.

Figure 8:
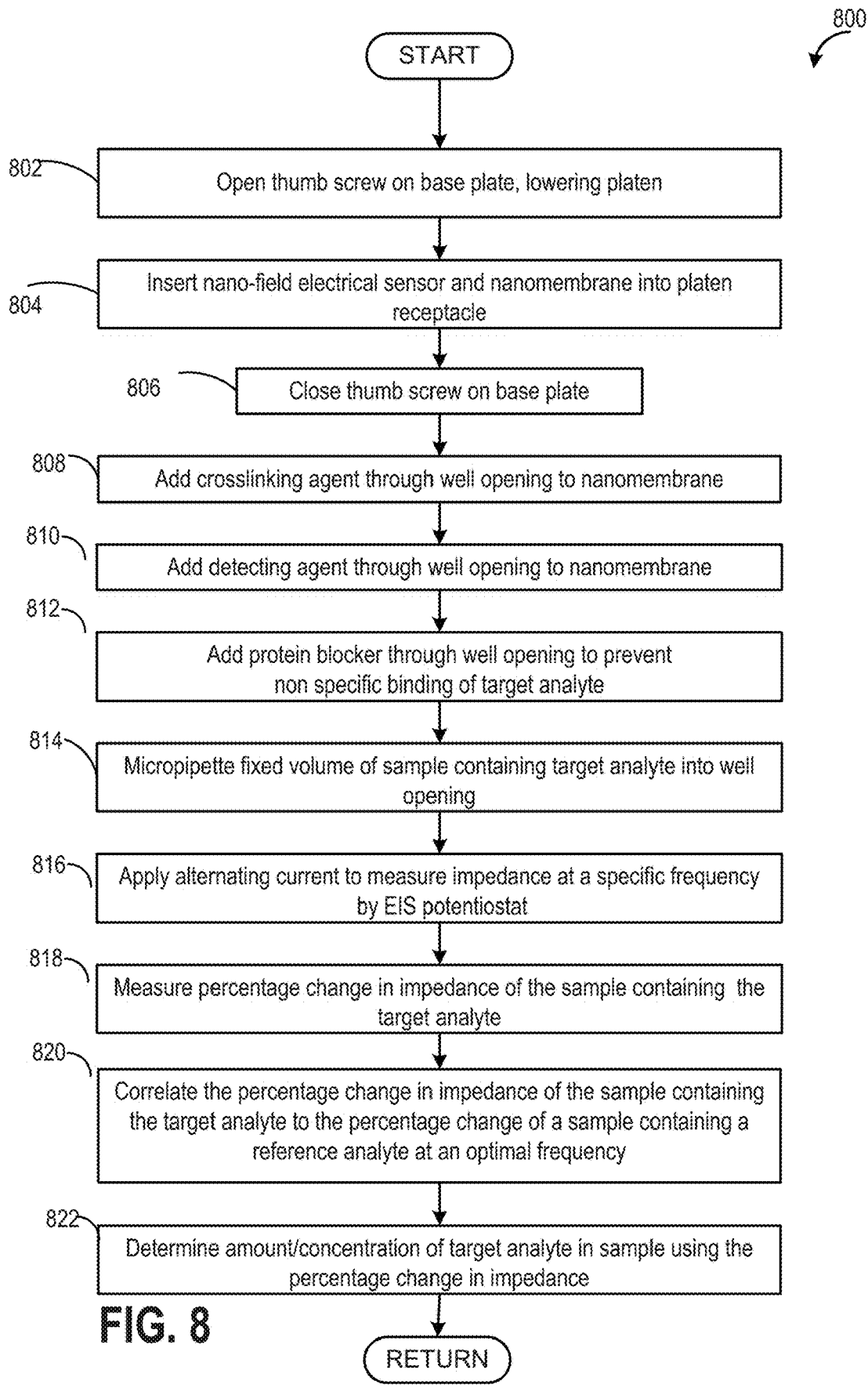
FIG. 8 is a simple flow diagram illustrating the method of detection of target analytes using the composition with the nano-field electrical sensor described herein.

Turning now to FIG. 8, a simple flow diagram 800 illustrating the method of detection of target analytes using the composition with the nano-field electrical sensor described herein is shown. At 802, method 800 opens the thumb screw (e.g. thumb screw 204) positioned on the base plate. The thumb screw may be positioned centrally on the top of the base plate that may withstand vibrations and a pressure of 1-2 lbs. The sensor and nanoporous membrane are placed on the platen 804, and the thumb screw is closed 806. At 808 cross linking agents are added through the manifold opening into a well and to the nanoporous membrane. The cross linking agent may be any suitable cross-linking agent. In one example, the cross linking agent is DTSP as shown at 402 in FIG. 6 and FIG. 7. The cross linking agent may be introduced into the composition via openings on the acrylic manifold. The cross linking agent may adhere to or coat the nanoporous membrane. At 806 at least one detecting agent is added through the manifold opening to a well over the nanoporous membrane. In one example, the detecting agent may be an antibody that binds to the cross linking agent when introduced through the manifold opening onto the nanoporous membrane. At 812, a protein blocker is added through the well opening that may adhere to the unbound cross linkers to prevent any non-specific binding of target analyte. The protein blocker may also bind to any voids in the nanoporous membrane and/or nonspecific sites (also known as reactive sites). In the examples mentioned above, the protein used as a blocker may be any protein that does not bind specifically to one or more target analytes. In this way, the membrane maybe functionalized and primed for target analyte detection. At 814, a fixed volume of the sample comprising the target analyte may be micropipetted into the opening on the manifold. The volume of sample needed for detection of target analytes of interest may be a very small volume e.g. a droplet in the range of 50-100 microliters. At 816, an alternating current may be applied to measure impedance at a specific frequency by the EIS potentiostat. Optimal frequencies for identifying and quantifying the target sample may be determined by any means generally used. In one example, current is passed through the contacts on the base substrate over a range of frequencies, (e.g. a sweep of frequencies) to determine the point of greatest percentage change in impedance. In some embodiments, the sweep of frequencies may range from about 0.01-100.00 Hz. The optimal frequency for a target analyte may be determined for each target analyte. In some embodiments, the impedance generated by each nanopore may be summed to produce a single signal. A sample containing the unknown presence or quantity of the analyte of interest is then tested at the optimized frequency. At 818 the percentage change in impedance of a sample containing the specific target analyte is measured. At 820, a percentage change in impedance of a sample containing the specific target analyte is compared to a dose response curve showing percentage change in impedance for a reference and the presence and concentration of the target analyte is correlated 822. The presence of one or more target analytes in a sample including 1, 2, 3, 4, 5, 6, 7, 8, 9, 10, 11, 12, 13, 14, 15 or more target analytes may be determined using the optimal unique frequency for each of those target analytes. In one example, the composition may be a hand-held EIS reader and may be utilized at point of care for rapid results. In some embodiments, reference frequencies are determined for a plurality of analytes and series of reference frequencies applied one at a time may be used to determine the amount and/or presence of a plurality of target analytes in a sample. In further embodiments, a combination of analytes may be used in a reference sample to determine the presence or absence of a plurality of analytes. For example, in the case of heart attack, both Troponin I and Troponin T biomarkers may be present in a sample obtained from a patient. Determining the concentration of both Troponin I and Troponin T in a sample may be accomplished using a reference sample containing both analytes. In some embodiments, diagnostic accuracy of biomarkers may be improved by testing for a combination of suspected target analytes in a sample whether the testing is for each analyte individually for a combination of target analytes tested together.

The present technology further provides a kit for detecting biomarkers and other target analytes. In some embodiments, a kit may be designed to test for a specific biomarker or target analyte. In other embodiments, a kit may be designed to test for a series of target analytes. In further embodiments, the kit will comprise a nano-electrical sensor with a base substrate and functionalization nanoporous membrane appropriate for a particular target analyte and a method for holding the nanoporous membrane in place such as an alumina manifold with one or more openings. The kit may further comprise printed instructions for appropriate sample type and placement and/or a reference result. The kit may additionally provide interpretations of results, either as the presence or absence of target analyte detected or as a diagnosis of the pathological condition.

For example, a nanoporous membrane designed to detect Troponin may have a substrate with a nanoporous membrane of a porosity of 45-50% with 200 nm pores. The parameters of interest that would be inputted include an applied AC voltage of 10 mV and an applied frequency in the optimized range of 100-150 KHz. Using the compositions described herein, troponin may be measured at 500 to 5000 times more sensitivity than currently existent methods, with a limit of detection of 0.009 ng/L.

The terminology used herein is for the purpose of describing particular embodiments only and is not intended to be limiting of the invention. As used in this document, the singular forms "a," "an," and "the" include plural references unless the context clearly dictates otherwise. Unless defined otherwise, all technical and scientific terms used herein have the same meanings as commonly understood by one of ordinary skill in the art.

References to "one embodiment" or "an embodiment" do not necessarily refer to the same embodiment, although they may. Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively, unless expressly limited to a single one or multiple one. Additionally, the words "herein," "above," "below" and words of similar import, when used in this application, refer to this application as a whole and not to any particular portions of this application. When the claims use the word "or" in reference to a list of two or more items, that word covers all of the following interpretations of the word: any of the items in the list, all of the items in the list and any combination of the items in the list, unless expressly limited to one or the other.

EXAMPLES

The nano-field electrical sensor and methods of using it will now be described in greater detail with reference to the following examples. It should be appreciated by those of skill in the art that many changes can be made in the specific embodiments that are disclosed and still obtain a like or similar result without departing from the spirit and scope of the invention.

Example 1

Construction of Nano-Field Electrical Sensor

An exemplary assembled nano-field electrical sensor is shown in FIG. 3 at 300. An alumina base substrate was cleaned with 100% isopropyl alcohol followed by 1 mL of deionized water and air dried. Then, a working, counter and reference electrode were deposited on the first surface of the alumina base substrate by vapor deposition. The working and counter electrodes were gold, while the reference electrode was silver, all of a purity of 99.9%.

Example 2

Vapor Deposition of Electrode Material

A base substrate comprising alumina of about 4.25×4.25" and 0.040" thick was wiped down with isopropyl alcohol. The alumina plate was placed in a vacuum chamber, which was evacuated. A shadow mask for the silver (reference) electrode was magnetically attached to the alumina plate. The plate/mask combination was sputter etched with argon gas for two minutes. 500 Å of titanium was deposited. 1000 Å of silver was then deposited. The chamber was then opened and the silver shadow mask was removed.

A shadow mask of the pattern of the gold electrode was placed over the silver electrode on the base material and aligned with two edges. The aligned mask/plate was placed onto a 5" by 5" magnetic chuck. 500 Å of titanium was melted in a vacuum and sputter deposited onto the base material in a vacuum chamber containing argon gas introduced at a pressure of 10 mtorr. 2000 Å of gold was then applied over the titanium.

Example 3

Functionalizing the Nanoporous Membrane

A nanoporous membrane was placed on the base substrate over the gold counter electrode, gold working electrode, and silver reference electrode. Two nested O-rings were attached to the bottom of the manifold and the manifold was then placed over the nanoporous membrane with the O-rings in contact with the nanoporous membrane and bound to the nanoporous membrane/electrode/base substrate using pressure. Dithobis succinimidyl propinate (DSP) was dissolved in dimethyl sulfoxide (DMSO) to prepare a 20 mM solution. The DSP was then micropipetted through a hole in the manifold and into a well to reach the nanoporous membrane. The base substrate/electrode/nanoporous membrane/manifold composition was then incubated with the DSP for 30 minutes at room temperature. Excess DSP was then removed using 200 mL of DMSO wash. 100 ng/ml of detecting agent was then micropipetted into the holes of the manifold to a well to reach the nanoporous membrane. The composition with the DSP and detecting agent was then incubated at room temperature for 60 minutes. After 60 minutes, the base substrate/electrodes/nanoporous membrane/O-ring/manifold composition with DSP and detecting agent was then washed with a PBS (phosphate buffered saline) three times. The base substrate the base substrate/electrodes/nanoporous membrane/O-ring/manifold composition was then treated with Superblock™ (PBS, Thermo-Fischer, Waltham, Mass., USA) for 60 minutes. The device was then washed with PBS and allowed to dry.

Example 4

Dose Response Study of Green Fluorescent Protein

A dose response study was carried out using samples containing GFP and samples containing negative controls (Troponin T). The study was carried out using the nano-field electric sensor described in Example 1 and the process described in Example 3. A base substrate comprising a gold electrode was overlain with 200 nm nylon nanoporous membrane and an alumina manifold was sealed in place. The nanoporous membrane base substrate combination was then treated with dithobis succinimidyl propinate (DSP) dissolved in dimethyl sulfoxide (DMSO) to prepare 20 mM solution and incubated for 20 minutes. Excess DSP was then removed using 100 microliter DMSO wash once. The base substrate-nanoporous membrane-DSP was then incubated with 100 ng of green fluorescent protein antibody (GFP) for 60 minutes. After 60 minutes, the base substrate-nanoporous membrane-DSP-GFP was treated with Superblock™ (PBS, Thermo-Fischer, Waltham, Mass., USA) for 60 minutes. The device was then washed with PBS and impedance measured to determine a baseline noise.

Figure 9:
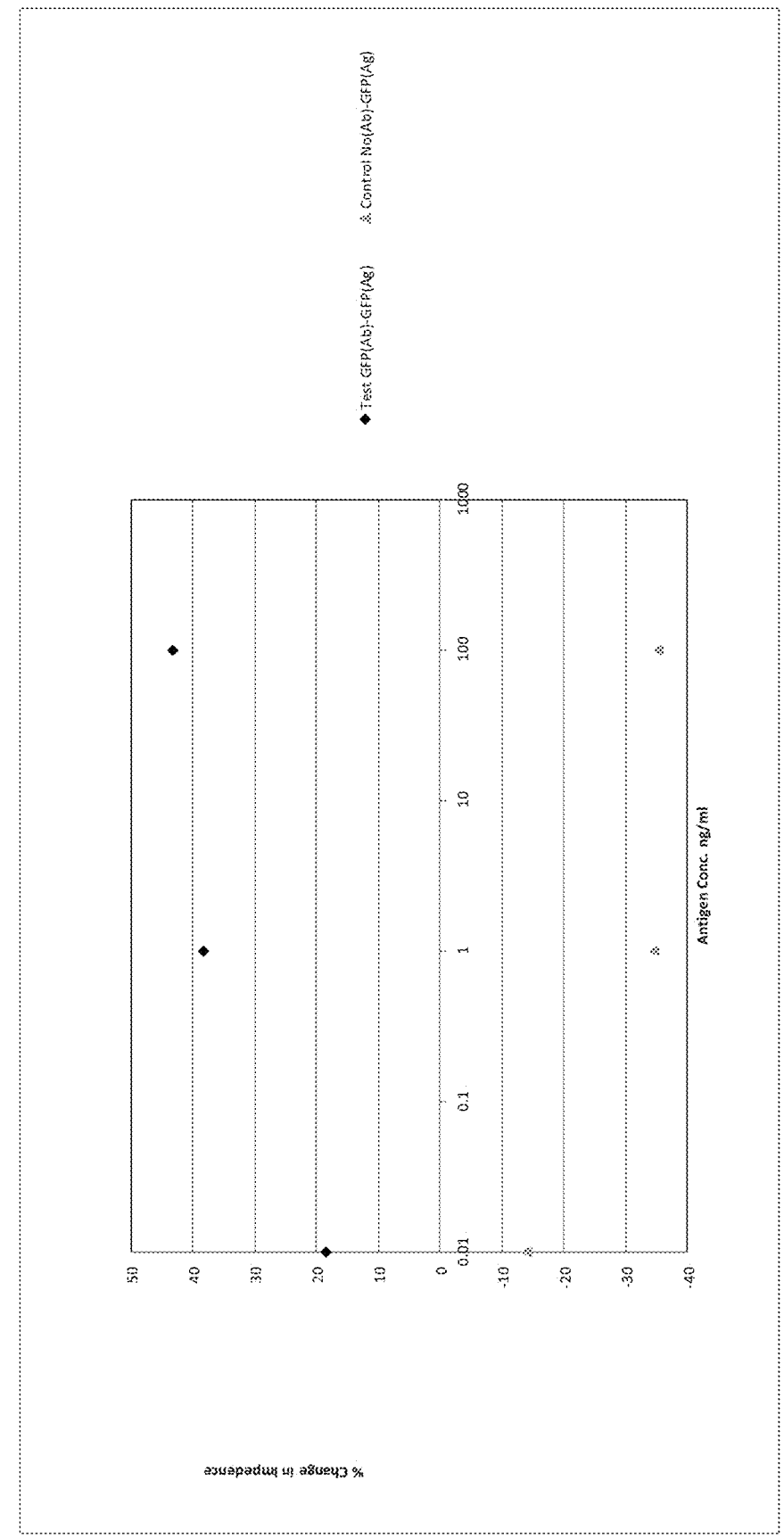
FIG. 9 is a graph depicting green fluorescent protein (GFP) antigen impedance response.

A sample comprising GFP in PBS was then added through the openings in the manifold for 15 minutes and the impedance of the sensor comprising the target analyte was measured. As shown in FIG. 9, a dose response curve is identified between a percentage change of impedance and increased amounts of GFP (diamond) in comparison to samples which contained a control (triangle). For the negative control, no antibody was attached to the nanoporous membrane, and the sample contained GFP antigen. As seen in the negative control (non-specific binding), the change in impedance decreased in the opposite direction of the correct (specific binding) of the GFP antibody and the GFP antigen.

Example 5

Dose Response Curve for Troponin T

A dose response study was carried out using samples containing Troponin T. The study was carried out using the nano-field electric sensor described in Example 1 and the process described in Example 3. A base substrate comprising a gold electrode was overlain with 200 nm nylon nanoporous membrane and sealed with an alumina manifold. The nanoporous membrane base substrate combination was then treated with dithobis succinimidyl propinate (DSP) dissolved in dimethyl sulfoxide (DMSO) to prepare 20 mM solution and incubated for 20 minutes. Excess DSP was then removed using 100 microliter DMSO wash once. The base substrate-nanoporous membrane-DSP was then incubated with 100 ng of the Troponin T antibody for 60 minutes. After 60 minutes, the base substrate-nanoporous membrane-DSP-Troponin T antibody was treated with Superblock™ (PBS, Thermo-Fischer, Waltham, Mass., USA) for 60 minutes. The device was then washed with PBS and impedance measured to determine the baseline noise.

Figure 10:
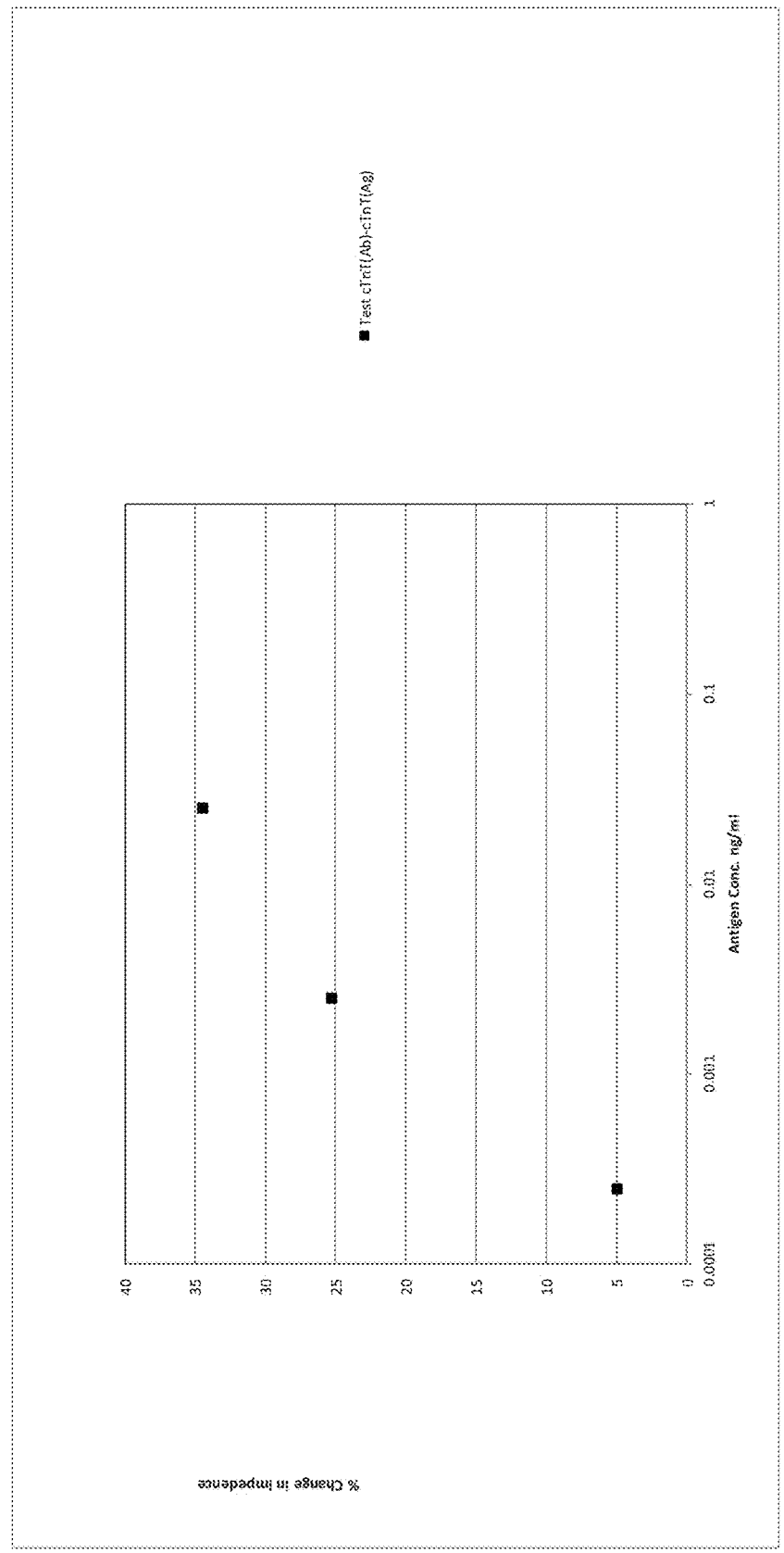
FIG. 10 is a graph of a dose response curve for Troponin T analyte concentration compared to change in impedance using the nano-field electrical sensor described herein.

A composition comprising Troponin T (TNT) antigen in PBS was then added into the processing spaces in the manifold for 15 minutes and the impedance of the sensor comprising the target analyte was measured. As shown in FIG. 10, a dose response curve is identified between a percentage change of impedance and increased amounts of Troponin T (square) in comparison to samples which contained a control (triangle).

Example 6

Dose Response Curve Zika Virus (NS I)

A dose response study was carried out using samples containing Zika virus (NS I). The study was carried out using the nano-field electric sensor described in Example 1 and the process described in Example 3. A base substrate comprising a gold electrode was overlain with 200 nm nylon nanoporous membrane and sealed together with an alumina manifold. The nanoporous membrane-base substrate combination was then treated with dithobis succinimidyl propinate (DSP) dissolved in dimethyl sulfoxide (DMSO) to prepare 20 mM solution and incubated for 20 minutes. Excess DSP was then removed using a 100 microliter DMSO wash once. The base substrate-nanoporous membrane-DSP was then incubated with 100 ng of the antibody for Zika virus NS I for 60 minutes. After 60 minutes, the base substrate-nanoporous membrane-DSP-Zika virus NS I antibody was treated with Superblock™ (PBS, Thermo-Fischer, Waltham, Mass., USA) for 60 minutes. The device was then washed with PBS and impedance measured to determine the baseline.

Figure 11:
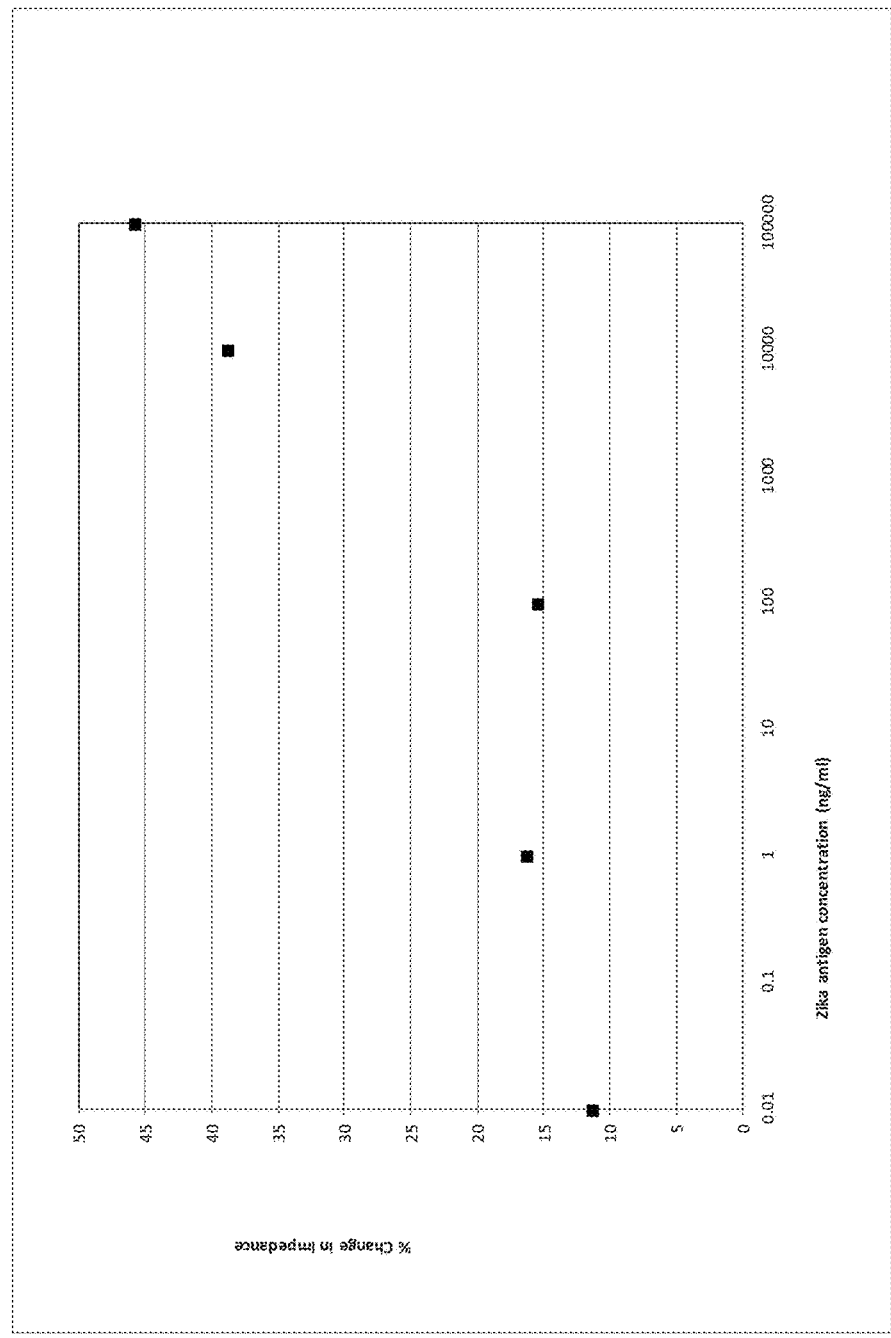
FIG. 11 is a graph depicting a dose dependent change in impedance for Zika virus NS I analyte concentration using the nano-field electrical sensor described herein.

A sample comprising Zika virus NS 1 antigen in PBS was then added into the processing spaces in the manifold and allowed to rest for 15 minutes. The impedance of the sensor comprising the target analyte was measured. As shown in FIG. 11, a dose response curve is identified between a percentage change of impedance and increased amounts of Zika virus NS 1 antigen (squares).

Example 7

Dose Response Curve Lyme (OspC Antigen)

A dose response study was carried out using samples containing Lyme (OspC antigen). The study was carried out using the nano-field electric sensor described in Example 1 and the process described in Example 3. A base substrate comprising a gold electrode was overlain with 200 nm nylon nanoporous membrane and sealed together with an alumina manifold. The nanoporous membrane-base substrate combination was then treated with dithobis succinimidyl propinate (DSP) dissolved in dimethyl sulfoxide (DMSO) to prepare 20 mM solution and incubated for 20 minutes. Excess DSP was then removed using a 100 microliter DMSO wash once. The base substrate-nanoporous membrane-DSP was then incubated with 100 ng of the antibody for Lyme, OspC for 60 minutes. After 60 minutes, the base substrate-nanoporous membrane-DSP-Lyme OspC antibody was treated with Superblock™ (PBS, Thermo-Fischer, Waltham, Mass., USA) for 60 minutes. The device was then washed with PBS and impedance measured by the potentiostat to determine the baseline noise.

Figure 12:
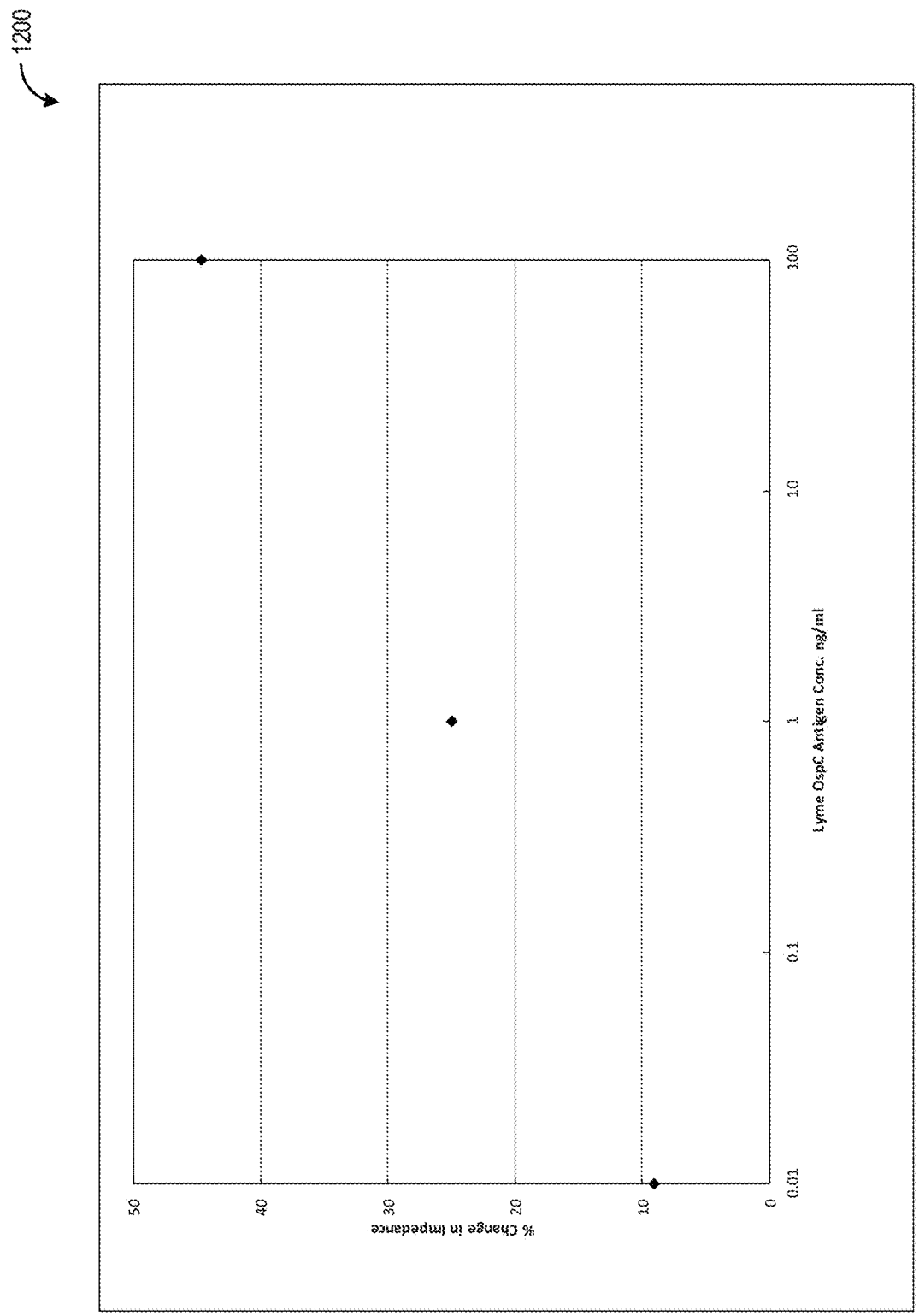
FIG. 12 is a graph depicting a dose dependent change in impedance for Lyme OspC antigen analyte concentration using the nano-field electrical sensor described herein.

A sample comprising Lyme OspC antigen in PBS was then added into the processing spaces in the manifold and setup was allowed to rest for 15 minutes. The impedance of the sensor comprising the target analyte was measured. As shown in FIG. 12, a dose response curve is identified between a percentage change of impedance and increased amounts of Lyme OspC antigen (diamonds).

Example 8

Dose Response Curve Lyme (VlsE Antibody)

A dose response study was carried out using samples containing Lyme (VlsE Antibody). The study was carried out using the nano-field electric sensor described in Example 1. The process was carried out as described in Example 3 with a few modifications as described herein. Following incubation of the membrane with DSP for 30 minutes at room temperature, excess DSP is removed using 200 mL of DMSO wash. The base substrate 104 and nanoporous membrane 202 linked with DSP is then incubated at room temperature with 100 ng/ml of VlsE antigen for 60 minutes. After 60 minutes, the base substrate 104, nanoporous membrane 202 device, with DSP and the linked VlsE antigen is then washed with a PBS (phosphate buffered saline) three times to remove any unbound antigen that may interfere with results. The base substrate 104 and nanoporous membrane 202 is then treated with Superblock™ (PBS, Thermo-Fischer, Waltham, Mass., USA) for 60 minutes. The device is then washed with PBS and impedance is measured to determine a baseline in the absence of the antibody of interest. The device was then washed with PBS and impedance measured by the potentiostat to determine the baseline (noise).

Figure 13:
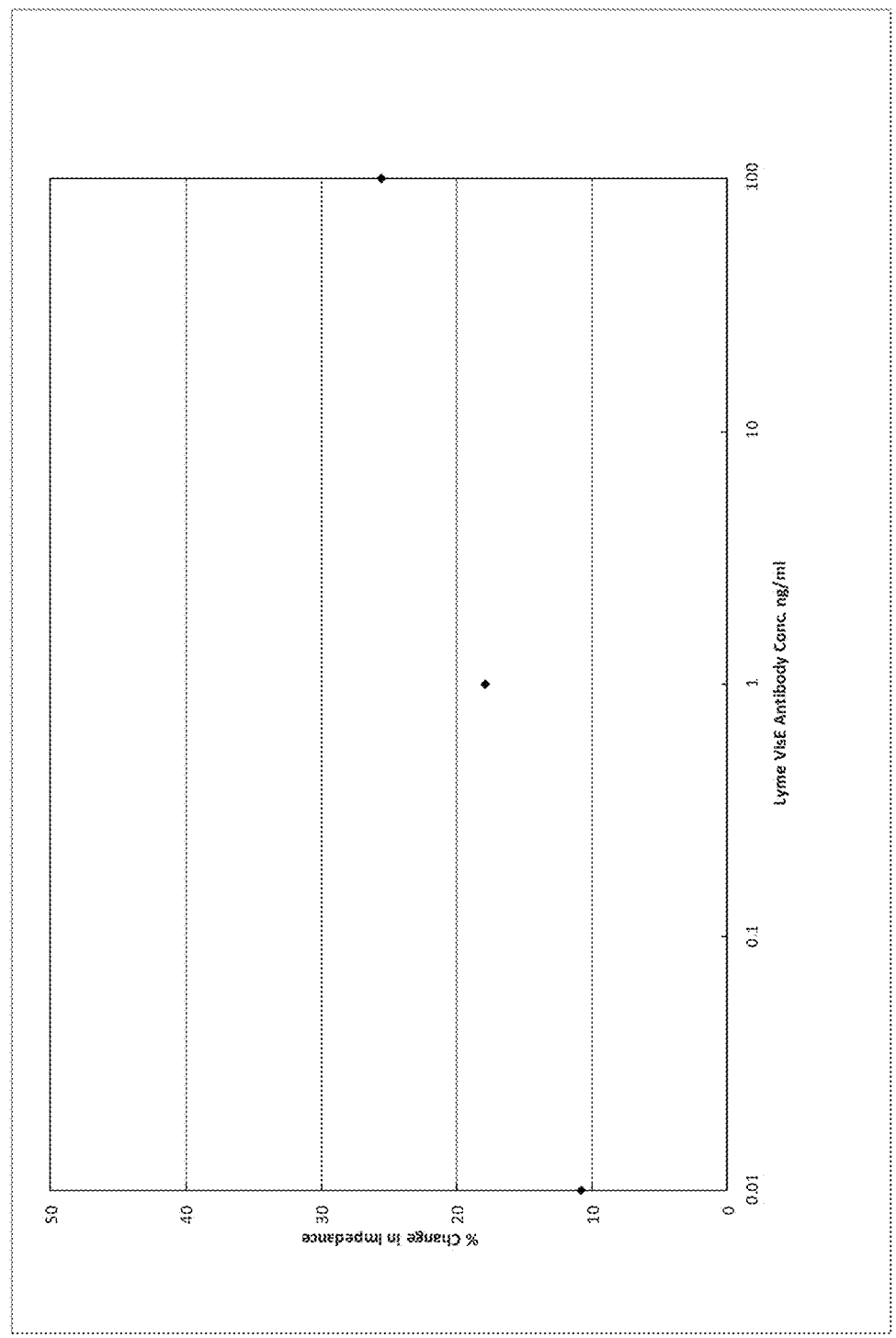
FIG. 13 is a graph depicting a dose dependent change in impedance for Lyme VlsE antibody concentration using the nano-field electrical sensor described herein.

A sample comprising Lyme VlsE antibody (not antigen) in PBS was then introduced into the processing spaces in the manifold and the setup was allowed to rest for 15 minutes. The impedance of the sensor comprising the target analyte was measured. As shown in FIG. 13, a dose response curve is identified between a percentage change of impedance and increased amounts of Lyme VlsE antibody (diamonds).

Example 9

Dose Response Curve for *Staphylococcus* Antigen

A dose response study was carried out using samples containing an antigen from *Staphylococcus* bacterium. The study was carried out using the nano-field electric sensor described in Example 1 and the process described in Example 3. A base substrate comprising a gold electrode was overlain with 200 nm nylon nanoporous membrane and sealed with an alumina manifold. The nanoporous membrane base substrate combination was then treated with dithobis succinimidyl propinate (DSP) dissolved in dimethyl sulfoxide (DMSO) to prepare 20 mM solution and incubated for 20 minutes. Excess DSP was then removed using 100 microliter DMSO wash once. The base substrate-nanoporous membrane-DSP was then incubated with 100 ng of the antibody for the *Staphylococcus* antigen for 60 minutes. After 60 minutes, the base substrate-nanoporous membrane-DSP-Staph. Antibody was treated with Superblock™ (PBS, Thermo-Fischer, Waltham, Mass., USA) for 60 minutes. The device was then washed with PBS and impedance measured to determine the baseline noise.

Figure 14:
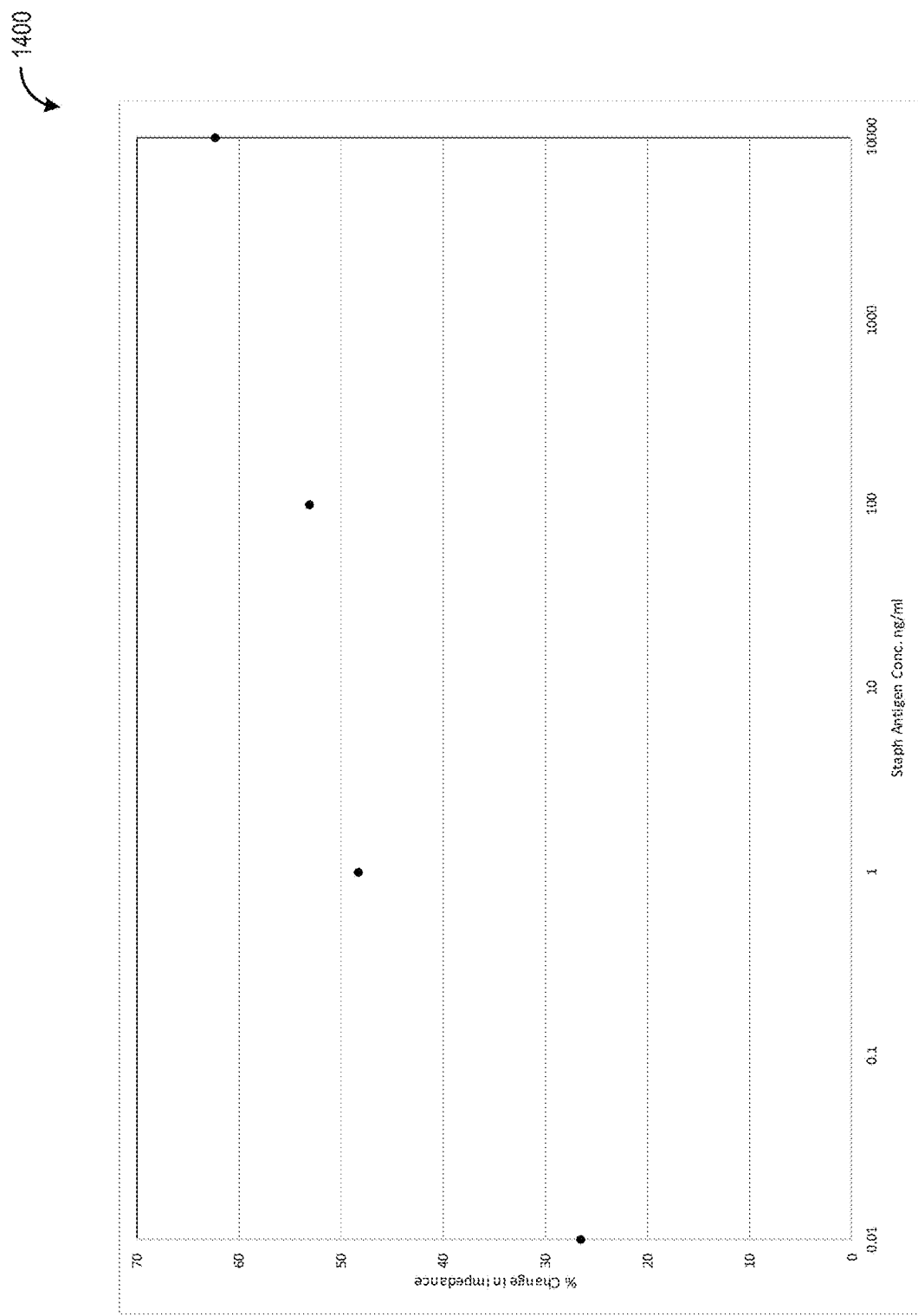
FIG. 14 is a graph depicting a dose dependent change in impedance for *Staphylococcus* antigen analyte concentration using the nano-field electrical sensor described herein.

A composition comprising antigen of *Staphylococcus* in PBS was then added into the processing spaces in the manifold for 15 minutes and the impedance of the sensor comprising the target analyte was measured. As shown in FIG. 14, a dose response curve is identified between a percentage change of impedance and increased amounts of antigen of *Staphylococcus* (circles).

While the compositions and methods of this invention have been described, it will be apparent to those of skill in art that variations may be applied to the methods and in the steps or in the sequence of steps of the method described herein without departing from the concept, spirit and scope of the invention. It will be apparent that certain agents which are either or both chemically or physiologically related may be substituted for the agents described herein while the same or similar results and/or conclusions may be determined. All such substitutions and modifications apparent to those skilled in the art are deemed to be within the spirit, scope and concept of the invention as defined by the appended claims.

The foregoing described aspects depict different components contained within, or connected with different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality.

The invention claimed is:

1. A method for detecting a target analyte in a sample comprising:
    placing an electrospun nanoporous membrane on a sensor comprising a biocompatible base substrate having a top surface onto which at least two electrodes in a capacitive relationship have been placed;
    inserting the sensor into a receptacle on a testing platform, wherein the testing platform comprises a base plate with a cutout and a first recess at a first end, a manifold in the first recess, and a platen with the receptacle, wherein the receptacle is at a first end of the platen and directly below the first cutout at the first end of the base plate;
    depositing the sample suspected of containing the target analyte into a hole in the manifold;
    attaching a potentiostat to the sensor;
    applying an electrical current to the sensor;
    measuring an impedance of the sample; and
    comparing a percentage change of impedance of a reference sample with the target analyte.

2. The method of claim 1, wherein the target analyte is a plurality of analytes in the sample.

3. The method of claim 1, further comprising determining an amount of the target analyte present in the sample.

4. The method of claim 1, wherein an impedance in each pore of the electrospun nanoporous membrane is summed.

5. A testing platform for analyte detection comprising:
    a base plate on four legs with a cutout in a first end and a first recess in a bottom surface of the base plate;
    a manifold in the first recess of the base plate and affixed to the bottom surface of the base plate;
    a platen with a first receptacle at a first end with a second cutout in the first receptacle, wherein the platen and the base plate are parallel to one another in a horizontal plane and the platen is between the legs of the base plate;
    wherein the cutout in the first end of the base plate is over the first receptacle at the first end of the platen; and
    a thumb screw connected to a threaded rod, wherein the threaded rod passes through a first surface of the base plate, out a second surface of the base plate, through first and second surfaces of the platen, and through a compression spring in contact with the second surface of the platen, wherein the compression spring is held in place on the threaded rod by a thumb nut.

6. The testing platform of claim 5, wherein tightening the thumb screw pushes the platen down.

7. The testing platform of claim 5, wherein loosening the thumb screw raises the platen.

8. The testing platform of claim 5, wherein the manifold is affixed to the bottom surface of the first recess by at least one screw.

* * * * *